US011958841B2

(12) United States Patent
Palmese et al.

(10) Patent No.: US 11,958,841 B2
(45) Date of Patent: Apr. 16, 2024

(54) RENEWABLE HIGHLY BIOBASED POLYBENZOXAZINE THERMOSETS FOR COMPOSITE APPLICATIONS

(71) Applicants: DREXEL UNIVERSITY, Philadelphia, PA (US); The Government of the United States of America, as represented by The Secretary of the Army, Washington, DC (US)

(72) Inventors: Giuseppe R. Palmese, Hainesport, NJ (US); Santosh K. Yadav, Geneva, OH (US); John J. LaScala, Wilmington, DE (US)

(73) Assignees: Drexel University, Philadelphia, PA (US); The United States of America as represented by The Secretary of the Army, Washington, DC (US)

( * ) Notice: Subject to any disclaimer, the term of this patent is extended or adjusted under 35 U.S.C. 154(b) by 0 days.

(21) Appl. No.: 18/189,286

(22) Filed: Mar. 24, 2023

(65) Prior Publication Data
US 2024/0092767 A1 Mar. 21, 2024

Related U.S. Application Data

(62) Division of application No. 16/637,551, filed as application No. PCT/US2018/047184 on Aug. 21, 2018, now Pat. No. 11,643,406.

(60) Provisional application No. 62/547,952, filed on Aug. 21, 2017.

(51) Int. Cl.
| *C07D 413/06* | (2006.01) |
| *C07D 307/52* | (2006.01) |
| *C07D 413/14* | (2006.01) |
| *C08G 73/02* | (2006.01) |

(52) U.S. Cl.
CPC ......... *C07D 413/06* (2013.01); *C07D 307/52* (2013.01); *C07D 413/14* (2013.01); *C08G 73/024* (2013.01); *C08G 73/0273* (2013.01)

(58) Field of Classification Search
CPC ... C07D 413/06; C07D 307/52; C07D 413/14
See application file for complete search history.

(56) References Cited

U.S. PATENT DOCUMENTS

| 5,476,716 A | 12/1995 | Gallo |
| 6,225,440 B1 | 5/2001 | Ishida |
| 6,376,080 B1 | 4/2002 | Gallo |

FOREIGN PATENT DOCUMENTS

| CN | 106674214 A | 5/2017 |

OTHER PUBLICATIONS

Baroncini, Elyse A., et al. "Recent advances in bio-based epoxy resins and bio-based epoxy curing agents." Journal of Applied Polymer Science 133.45 (2016).
Dumas, Ludovic, et al. "Eugenol-based benzoxazine: from straight synthesis to taming of the network properties." Journal of Materials Chemistry A 3.11 (2015): 6012-6018.
Froimowicz, Pablo, et al. "Smart, Sustainable, and Ecofriendly Chemical Design of Fully Bio-Based Thermally Stable Thermosets Based on Benzoxazine Chemistry." ChemSusChem 9.15 (2016): 1921-1928.
Ghosh, N. N., B. Kiskan, and Y. Yagci. "Polybenzoxazines-new high performance thermosetting resins: synthesis and properties." Progress in Polymer Science 32.11 (2007): 1344-1391.
Hu, Fengshuo, et al. "Preparation and Characterization of Fully Furan-Based Renewable Thermosetting Epoxy-Amine Systems." Macromolecular Chemistry and Physics 216.13 (2015): 1441-1446.
Kotzebue, Lloyd Ryan Viana, et al. "Spectral and thermal studies on the synthesis and catalyzed oligomerization of novel cardanol-based benzoxazines." Polymer 92 (2016): 189-200.
Lligadas, Gerard, et al. "Polybenzoxazines: new players in the bio-based polymer arena." Polymer Chemistry 5.23 (2014): 6636-6644.
Puchot, L., et al. "Breaking the symmetry of dibenzoxazines: a paradigm to tailor the design of bio-based thermosets." Green Chemistry 18.11 (2016): 3346-3353.
Sini, N. K., Jayashree Bijwe, and Indra K. Varma. "Renewable benzoxazine monomer from Vanillin: Synthesis, characterization, and studies on curing behavior." Journal of Polymer Science Part A: Polymer Chemistry 52.1 (2014): 7-11.
Sini, N. K., Jayashree Bijwe, and Indra K. Varma. "Thermal behaviour of bis-benzoxazines derived from renewable feed stock 'vanillin'." Polymer Degradation and Stability 109 (2014): 270-277.
Takeichi, Tsutomu, Takehiro Kawauchi, and Tarek Agag. "High performance polybenzoxazines as a novel type of phenolic resin." Polymer journal 40.12 (2008): 1121.
Periyasamy, Thirukumaran, Shakila Parveen Asrafali, and Sarojadevi Muthusamy. "New benzoxazines containing polyhedral oligomeric silsesquioxane from eugenol, guaiacol and vanillin." New Journal of Chemistry 39.3 (2015): 1691-1702.
Thirukumaran, P., A. Shakila Parveen, and M. Sarojadevi. "Synthesis and copolymerization of fully biobased benzoxazines from renewable resources." ACS Sustainable Chemistry & Engineering 2.12 (2014): 2790-2801.
Wang, J., W. Liu, and T. Feng. "Furan-Based Benzoxazines." Advanced and Emerging Polybenzoxazine Science and Technology. 2017. 533-567.
Wang, CaiFei, et al. "Synthesis and copolymerization of fully bio-based benzoxazines from guaiacol, furfurylamine and stearylamine." Green Chemistry 14.10 (2012): 2799-2806.

(Continued)

*Primary Examiner* — Rebecca L Anderson
(74) *Attorney, Agent, or Firm* — Mendelsohn Dunleavy, P.C.

(57) ABSTRACT

Benzoxazine compounds, methods of making them, polymers made therefrom and methods of polymerizing the benzoxazines. These renewable benzoxazine monomers and polymers that utilize the variety of building blocks found in renewable plant biomass, demonstrate excellent processability and large temperature windows for processing of resin systems.

10 Claims, 8 Drawing Sheets

(56) References Cited

OTHER PUBLICATIONS

International Search Report and Written Opinion for corresponding international application No. PCT/US2018/047184; dated Mar. 26, 2019 (14 pages).

Liu, Ying-Ling et al., "High Performance Benzoxazine Monomers and Polymers Containing Furan Groups." Journal of Polymer Science Part A: Polymer Chemistry 43.21 (2005): 5267-5282.

Shen, Xiaobin, et al. "Synthesis of high performance polybenzoxazine networks from bio-based furfurylamine: Furan vs benzene ring." Polymer 122 (2017): 258-269.

Extended European Search Report for corresponding European application No. 18849100.5; dated Sep. 9, 2021 (11 pages).

Han, Yi-Jen, et al. "Radical and Atom Transfer Halogenation (RATH): A Facile Route for Chemical and Polymer Functionalization." Macromolecular Rapid Communications 37.10 (2016): 845-850.

RENEWABLE HIGHLY BIOBASED POLYBENZOXAZINE THERMOSETS FOR COMPOSITE APPLICATIONS

CROSS REFERENCE TO RELATED APPLICATIONS

This application is a divisional of U.S. patent application Ser. No. 16/637,551, filed on Feb. 7, 2020, which, in turn, is a 371 continuation of PCT/US2018/047184, filed on Aug. 21, 2018, which, in turn, claims the benefit of U.S. Provisional Application No. 62/547,952, filed on Aug. 21, 2017, the entire disclosure of which is hereby incorporated by reference as if set forth fully herein.

STATEMENT OF GOVERNMENT INTEREST

This invention was made with government support under Contract Number W911NF-15-2-0017 awarded by the United States Army Research Laboratory. The Government has certain rights in this invention.

FIELD OF THE INVENTION

The present invention relates to a series of the renewable benzoxazine monomers and polymers that utilizes the variety of building blocks found in renewable plant biomass, which demonstrate excellent processability and large temperature windows for processing of resin systems.

BACKGROUND

Benzoxazine monomers are the precursor for polybenzoxazine polymers [1]. Benzoxazines are a class of heterocyclic compounds based on a six-membered heterocycle bearing one oxygen and one nitrogen atoms fused to a single aromatic ring and typically synthesized through Mannich type condensation of phenols, amines (aliphatic or aromatic) and formaldehyde or formaldehyde precursors (i.e. paraformaldehyde) without any catalysts [1-3]. Polybenzoxazines possess unique advantages for example, low melt viscosity of the precursors, curing without a strong catalyst and nonvolatile release together with near-zero volumetric change during curing. The cured polybenzoxazines are characterized by high glass transition temperatures (Tg), low water absorption, high char yield, and excellent thermal and electrical properties [2]. Most of these outstanding properties are related to the presence of high density of inter- and intramolecular hydrogen bonding between the phenolic groups and the nitrogen containing Mannich-type bridges. Polybenzoxazines are an alternative to high-performance phenolic resins for high-temperature applications. The rising worldwide fossil fuel crisis and current health and environmental issues are the major challenges for polybenzoxazines in terms of supply and costs [2, 3]. Furthermore, petroleum does not easily afford a variety of chemical structures or functionality. Recent research efforts have focused on developing renewable alternatives to replace the phenol and amine monomers in benzoxazines [4, 5]. Plants composed of cellulose, hemicellulose, lignin, triglycerides, and other natural chemicals in complex combinations to sustain life and to withstand environmental stress factors [6] may include the needed components. These materials are characterized by distinct building blocks arranged and connected with appropriate chemical functionality so that the systems serve multiple needs such as chemical and microbial resistance, nutrient transport, energy, strength, and toughness. To overcome the limitations of petroleum-derived building blocks, we employed an approach to develop the renewable benzoxazine monomers and polymers inspired by nature that utilizes the variety of building blocks found in renewable plant biomass [5, 7-14].

The present invention sets forth a series of new, highly bio-derived, benzoxazine polymers, which demonstrate improved processability and properties, making them good candidates for replacement of some petroleum-based polymers. These renewable biomass-based polymer systems may be used in tunable-property for various applications due to the ability to combine different bio-based building blocks to yield polymers with the desired properties.

SUMMARY OF THE INVENTION

In accordance with the disclosure, exemplary embodiments provide benzoxazine compounds, methods of preparing the benzoxazine compounds, and polymers formed by benzoxazines.

The following are sentences describing embodiments of the invention.

1. A benzoxazine compound of Formula (I) or Formula (III), wherein Formula (I) has the following structure:

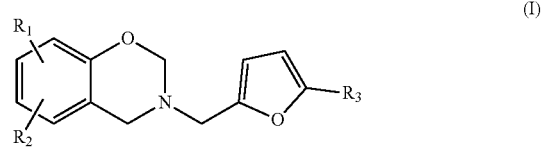

wherein $R_1$ and $R_2$ in Formula (I) may independently be selected from hydrogen, a straight or branched alkyl having 1-4 carbon atoms, a straight or branched alkenyl having 1-4 carbon atoms, a straight or branched alkoxy group having 1-4 carbon atoms and —C(=O)H; $R_3$ may be hydrogen or a group having Formula (II):

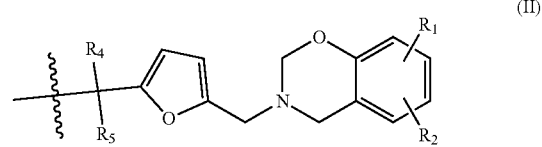

wherein $R_1$ and $R_2$ in Formula (II) may independently be selected from the same groups for $R_1$ and $R_2$ that are defined above,

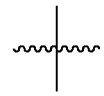

represents the bond to the ring carbon of the furan ring in Formula (I), and $R_4$ in Formula (II) may be selected from hydrogen an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms, $R_5$ in Formula (II) may be selected from hydrogen an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms, wherein $R_4$ and $R_5$ in Formula (II) cannot both be hydrogen;

wherein Formula (III) has the following structure:

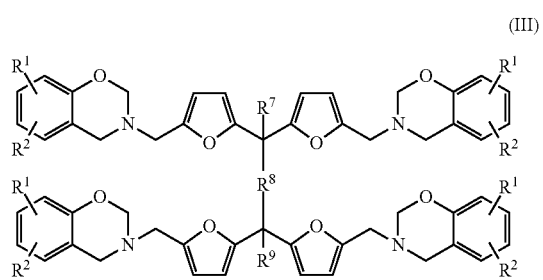

(III)

wherein $R^1$ and $R^2$ in Formula (III) may be independently selected from the same groups for $R^1$ and $R^2$ that are defined above, wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, optionally substituted aryl group having 6 to 15 carbon atoms and an optionally substituted cycloalkyl group having 3 to 12 carbon atoms; wherein the alkyl group, alkene group, heterocyclic group, aryl group, or cycloalkyl group can be substituted with 1 to 5 substituents independently selected from a halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted heterocyclic group with 3 to 15 carbon atoms, optionally substituted arylene group having 6 to 15 carbon atoms and an optionally substituted cycloalkylene group having 3 to 12 carbon atoms; wherein the alkylene group, alkenylene group, heterocyclic group, arylene group, or cycloalkylene group can be substituted with 1 to 4 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms.

2. The benzoxazine compound of the preceding sentence, wherein $R_1$ and $R_2$ of Formula (I) and $R_1$ and $R_2$ of Formula (III) may be independently selected from methyl, isopropyl, methoxy, —C(=O)H and —CH$_2$—CH=CH$_2$ and $R_3$ may be hydrogen.

3. The benzoxazine compound of any preceding sentence, wherein $R_3$ may be a group having Formula (II) and the benzoxazine compound may be symmetrical in that $R_1$ and $R_2$ of Formula (I) are identical to R1 and R2 of Formula (II), respectively.

4. The benzoxazine compound of any preceding sentence, wherein $R_1$ and $R_2$ of Formula (I) may not be hydrogen and are bonded at the 6-position and 8-position of the benzoxazine ring, respectively.

5. The benzoxazine compound of any one of sentences 1-3, wherein (a) $R_1$ and $R_2$ of Formula (I) may not be hydrogen and are bonded at the 6-position and 8-position of the benzoxazine ring, respectively, and $R_1$ and $R_2$ of Formula (II) are not hydrogen and are bonded at the 6-position and 8-position of the benzoxazine ring, respectively; or (b) $R_1$ and $R_2$ of Formula (I) are not hydrogen and are bonded at the 5-position and 8-position of the benzoxazine ring, respectively, and $R_1$ and $R_2$ of Formula (II) are not hydrogen and are bonded at the 5-position and 8-position of the benzoxazine ring, respectively.

6. The benzoxazine compound of sentence 1, wherein: $R_4$ and $R_5$ are each independently selected from hydrogen, an optionally substituted alkyl group having 7 to 20 carbon atoms, an optionally substituted alkene group having 3 to 20 carbon atoms, an optionally substituted cycloalkyl group having 3 to 12 carbon atoms and an optionally substituted phenyl group, wherein the alkyl group, alkene group, cycloalkyl group or phenyl group can be substituted with 1 to 5 substituents independently selected from an alkyl group having 1-10 carbon atoms, a hydroxyl group, and an alkoxy group having 1 to 20 carbon atoms, wherein both $R_4$ and $R_5$ cannot be hydrogen.

7. The benzoxazine compound of sentence 1, wherein $R_4$ may be hydrogen; $R_5$ may be a phenyl group which is optionally substituted with a hydroxyl group, an alkoxy group having 1 to 4 carbon atoms, an alkyl group having 1 to 6 carbon atoms, and an alkene group having 2 to 4 carbon atoms.

8. The benzoxazine compound of sentence 1, wherein $R_4$ and $R_5$ may be each independently selected from: hydrogen, an optionally substituted alkyl group having 8 to 18 carbon atoms, an optionally substituted alkene group having 4 to 18 carbon atoms, and an optionally substituted cycloalkyl group having 3 to 8 carbon atoms, wherein the alkyl group, alkene group, or cycloalkyl group can be substituted with 1 to 5 substituents independently selected from a halogen, hydroxy, amino, nitro, cyano, carboxy, an alkyl group having 1 to 8 carbons, and an alkoxy group having 1 to 8 carbon atoms; and wherein only one of $R_4$ and $R_5$ can be hydrogen.

9. The benzoxazine compound of sentence 1, wherein the benzoxazine may be
a) bis(5-((2H-benzo[e][1,3]oxazin-3(4H)-yl)methyl)furan-2-yl)methane;
b) 3,3'-((5,5'-methylenebis(furan-5,2-diyl))bis(methylene)) bis(8-methoxy-3,4-dihydro-2H-benzo[e][1,3]oxazine-6-carbaldehyde);
c) 3-(furan-2-ylmethyl)-5-isopropyl-8-methyl-3,4-dihydro-2H-benzo[e][1,3]oxazine;

d) bis(5-((5-isopropyl-8-methyl-2H-benzo[e][1,3]oxazin-3 (4H)-yl)methyl)furan-2-yl)methane; or e) bis(5-((6-allyl-8-methoxy-2H-benzo[e][1,3]oxazin-3 (4H)-yl)methyl)furan-2-yl)methane.

10. A method of forming the benzoxazine compound of Formula (I) of sentence 1, which may include reacting a furfurylamine compound, a formaldehyde compound, and a phenol compound.

11. The method of sentence 1, wherein the phenol compound may be selected from phenol, bisphenol A, bisguaiacol, vanillin, carvacrol, and eugenol.

12. The method of any one of sentences 10-11, wherein the furfurylamine compound may be a compound of Formula (IV) or a compound of Formula (V), wherein the compound of Formula (IV) is a difuran diamine compound having the following structure:

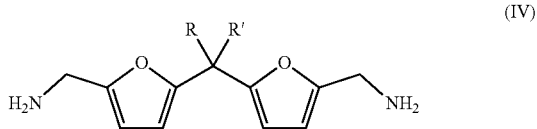

(IV)

wherein R and $R^1$ are independently selected from hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms, wherein only one of R and $R^1$ can be hydrogen;

wherein the compound of Formula (V) is a tetrafuran tetraamine compound with the following structure:

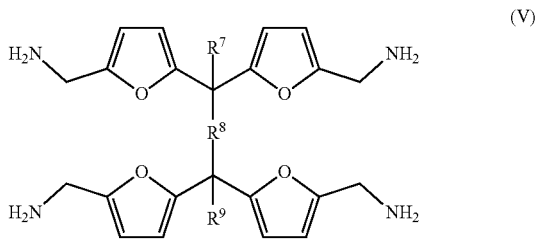

(V)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, optionally substituted aryl group having 6 to 15 carbon atoms and an optionally substituted cycloalkyl group having 3 to 12 carbon atoms; wherein the alkyl group, alkene group, heterocyclic group, aryl group, or cycloalkyl group can be substituted with 1 to 5 substituents independently selected from a halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted heterocyclic group with 3 to 15 carbon atoms, optionally substituted arylene group having 6 to 15 carbon atoms and an optionally substituted cycloalkylene group having 3 to 12 carbon atoms; wherein the alkylene group, alkenylene group, heterocyclic group, arylene group, or cycloalkylene group can be substituted with 1 to 4 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms.

13. The method of any one of sentences 10-12, wherein the formaldehyde compound is selected from formaldehyde and paraformaldehyde.

14. The method of sentence 10, wherein the method may further include an inert organic solvent, and heating a reaction mixture including the furfurylamine compound, the formaldehyde compound, and the phenol compound at temperatures between 60-85° C.

15. The method of sentence 14, wherein the inert organic solvent may be selected from an aliphatic or cycloaliphatic alcohol, an ester, a ketone, an aromatic or aliphatic hydrocarbon, a halogenated hydrocarbon and a mixture of one or more of the foregoing solvents.

16. The method of sentence 15, wherein the inert organic solvent may be a halogenated hydrocarbon selected from chloroform and methylene chloride.

17. A polymer formed by ring opening polymerization of at least benzoxazine compound of the Formula (I) or Formula (III) of sentence 1, and optionally including an epoxidation reaction with a diepoxide of the following Formula (VI):

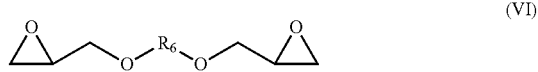

(VI)

wherein $R^6$ is an alkylene group having 1 to 20 carbon atoms, an alkenylene group having 2 to 20 carbon atoms, an heterocyclic group with 3 to 15 carbon atoms, an arylene group having 6 to 15 carbon atoms and a cycloalkylene group having 3 to 12 carbon atoms; wherein the alkylene group, alkenylene group, heterocyclic group, arylene group, or cycloalkylene group can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms.

18. A polymer formed by ring opening polymerization of at least one benzoxazine compound of the Formula (I) or Formula (III) of claim 1, and optionally including an epoxidation reaction with an epoxide selected from the group consisting of dibisphenol A epoxy resin, bisphenol F epoxy resin, novolac epoxy resin, aliphatic epoxy resin, glycidylamine epoxy resin, phenyl glycidyl ether, tetraglycidyl 4,4'-diaminodiphenylmethane, diepoxide having a phenylsulfone-phenyl group, and diglycidyl ether having a Bisphenol B, C, D, or E group.

19. The polymer of sentence 17 or 18, wherein the epoxy group-containing compound is a bisphenol-A diglycidyl ether (DGEBA) epoxy resin compound or an oligomer thereof.

20. A polymer including at least one repeating unit selected from a unit of Formula (VII) and a unit of Formula (VIII):

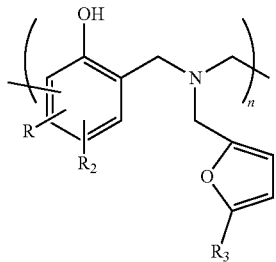

(VII)

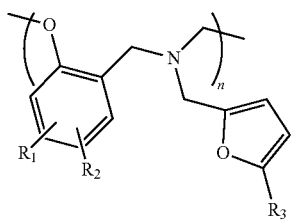

(VIII)

wherein $R_1$ and $R_2$ in Formulae (VII) and (VIII) are independently selected from hydrogen, a straight or branched alkyl, alkenyl, or alkoxy group having 1-4 carbon atoms and —C(=O)H, n is up to 1000; and $R^3$ is hydrogen, or at least one group of the Formula (II) as defined in claim 1, the Formula (IX) and the Formula (X):

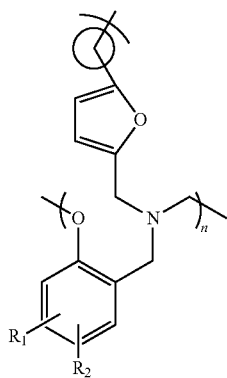

(IX)

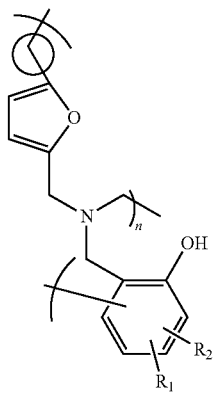

(X)

wherein $R_1$ and $R_2$ in Formulae (IX) and (X) are independently selected from hydrogen, a straight or branched alkyl, alkenyl, or alkoxy group having 1-4 carbon atoms and —C(=O)H, n is up to 1000, wherein the circled methylene group in Formula (IX) and Formula (X) is optionally substituted with $R_4$ and $R_5$ or $R_7$ and $R_9$ are as defined in sentence 1.

21. The compound or method or polymer of any one of sentences 1-20, wherein in $R_1$, $R_2$ and $R_3$ of Formula (I), $R_1$, $R_2$, $R_4$ and $R_5$ of Formula (II), $R_1$, $R_2$, $R_7$ and $R_9$ of Formula (III), R and $R_1$ of Formula (IV), $R_7$ and $R_9$ of Formula (V), $R_1$, $R_2$ and $R_3$ of Formula (VII), $R_1$, $R_2$ and $R_3$ of Formula (VIII), $R_1$ and $R_2$ of Formula (IX), and $R_1$ and $R_2$ of Formula (X):

the alkyl group is selected from a straight or branched chain butyl, pentyl, hexyl, heptyl, octyl, nonyl, decyl, undecyl and dodecyl, the alkene group is selected from a vinyl, propenyl, or a straight or branched chain butenyl, pentenyl, hexenyl, heptenyl, octenyl, nonenyl, decenyl, undecenyl and dodecenyl, the cycloalkyl group is selected from a cyclopentyl or cyclohexyl, the aryl group is selected from phenyl, tolyl, and biphenyl, the heterocyclic group is selected from pyrrolidine, pyrrole, tetrahydrofuran, furan, tetrahydrothiophene, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, piperidine, pyridine, bipyridine, tetrahydropyran, pyran, piperazine, diazines, morpholine, oxazine, thiomorpholine, and thiazine; and wherein in $R^5$ of Formula (III), $R^5$ of Formula (V), and $R^6$ of Formula (VI):

the alkylene group is selected from a straight or branched chain butylene, pentylene, hexylene, heptylene, octylene, nonylene, decylene, undecylene and dodecylene, the alkenylene group is selected from a vinylene, propenylene, or a straight or branched chain butenylene, pentenylene, hexenylene, heptenylene, octenylene, nonenylene, decenylene, undecenylene and dodecenylene, the cycloalkylene group is selected from a cyclopentylene or cyclohexylene, the arylene group is selected from phenylene, tolylene, and biphenylene; and wherein the groups may be optionally substituted with 1-4 substituents and the optional substituents are selected from the group consisting of an alkyl group having 1 to 3 carbons, an aldehyde, a hydroxyl group and methoxy group.

22. A polymer composition including the polymer of any one of sentences 17-20, and further including one or more of fibers, clays, silicates, fillers, whiskers, pigments, corrosion inhibitors, flow additives, film formers, defoamers, coupling agents, antioxidants, stabilizers, flame retardants, reheating aids, plasticizers, flexibilizers, anti-fogging agents, nucleating agents, or combinations thereof.

23. The polymer composition according to sentence 22, including the pigment, the corrosion inhibitor and the fibers and wherein the pigment is selected from titanium dioxide, iron oxides, carbon black and mixtures thereof; the corrosion inhibitor is zinc phosphate; and the fibers are glass fibers.

24. The polymer of any one of sentences 17-23, wherein the glass transition temperature ranges from 100° C. to 300° C., or 120° C. to 280° C. or 170° C. to 275° C.

25. The polymer of any one of sentences 17-23, wherein the flexural modulus ranges from 2 GPa to 4 GPa at room temperature, or from 2.2 GPa to 3.8 GPa at room temperature, or from 2.5 GPa to 3.7 GPa at room temperature.

26. The polymer of any one of sentences 17-23, wherein the flexural strength is greater than 20 MPa at room temperature, or greater than 22 MPa at room temperature, or greater than 25 MPa at room temperature.

27. The polymer of any one of sentences 17-23, wherein the UL-94 flammability (standard of 2017) is a V-0 or a V-1 rating.

Additional details and advantages of the disclosure will be set forth in part in the description which follows, and/or may be learned by practice of the disclosure. The details and advantages of the disclosure may be realized and attained by means of the elements and combinations particularly pointed out in the appended claims.

DETAILED DESCRIPTION OF THE PREFERRED EMBODIMENTS

Figure 1:
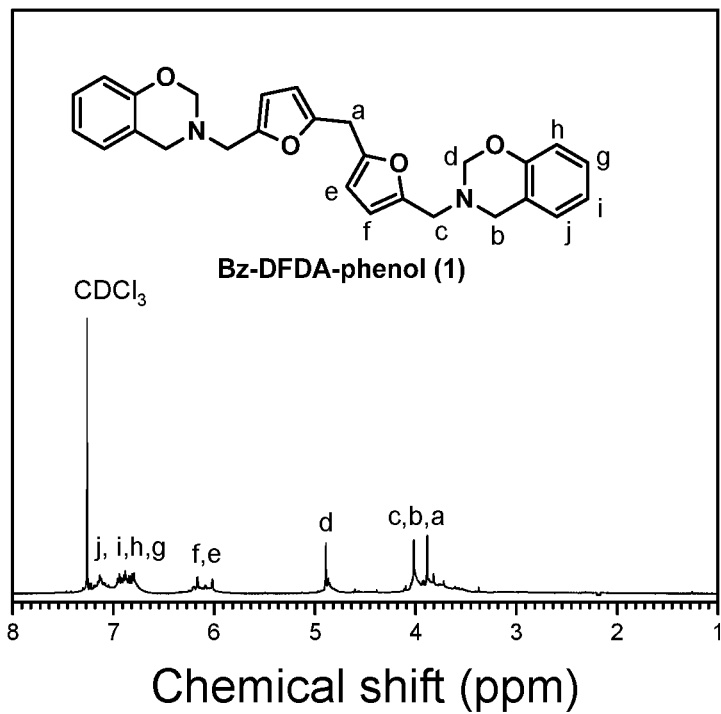
FIG. 1 shows the $^1$H-NMR spectrum of bis(5-((2H-benzo[e][1,3]oxazin-3(4H)-yl)methyl)furan-2-yl)methane; (BZ-DFDA-phenol).
Figure 2:
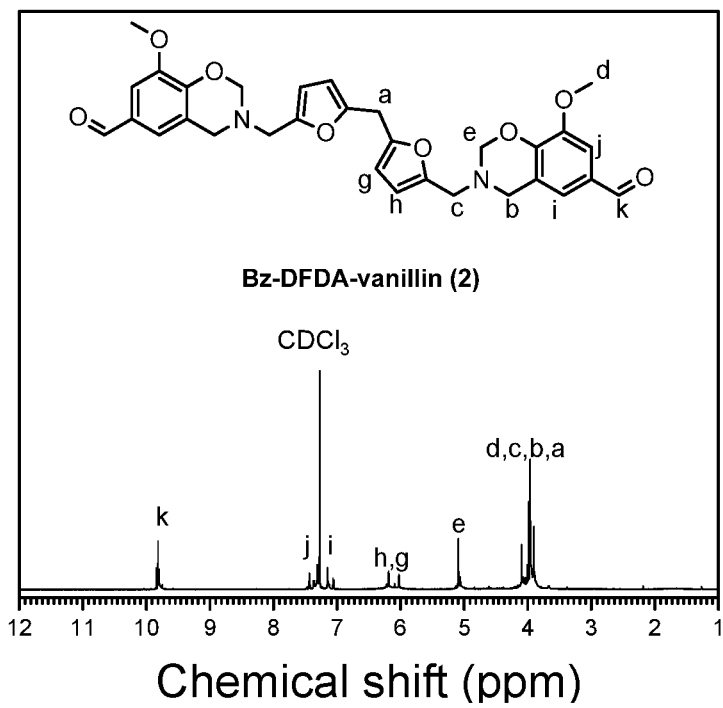
FIG. 2 shows the $^1$H-NMR spectrum of 3,3'-((5,5'-methylenebis(furan-5,2-diyl))bis(methylene))bis(8-methoxy-3,4-dihydro-2H-benzo[e][1,3]oxazine-6-carbaldehyde); (BZ-DFDA-vanillin).
Figure 3:
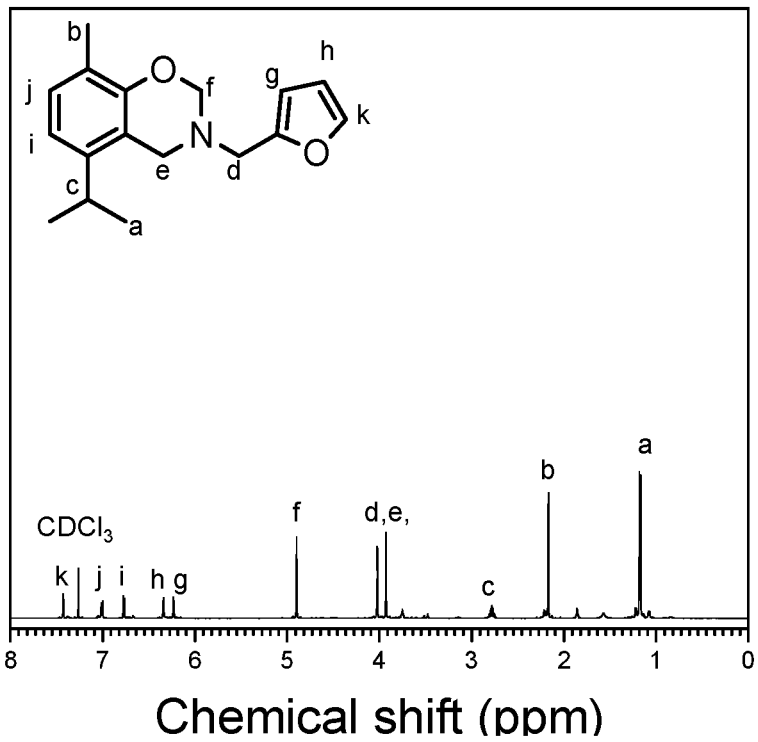
FIG. 3 shows the $^1$H-NMR spectrum of 3-(furan-2-ylmethyl)-5-isopropyl-8-methyl-3,4-dihydro-2H-benzo[e][1,3]oxazine; (Bz-FA-carvacrol).
Figure 4:
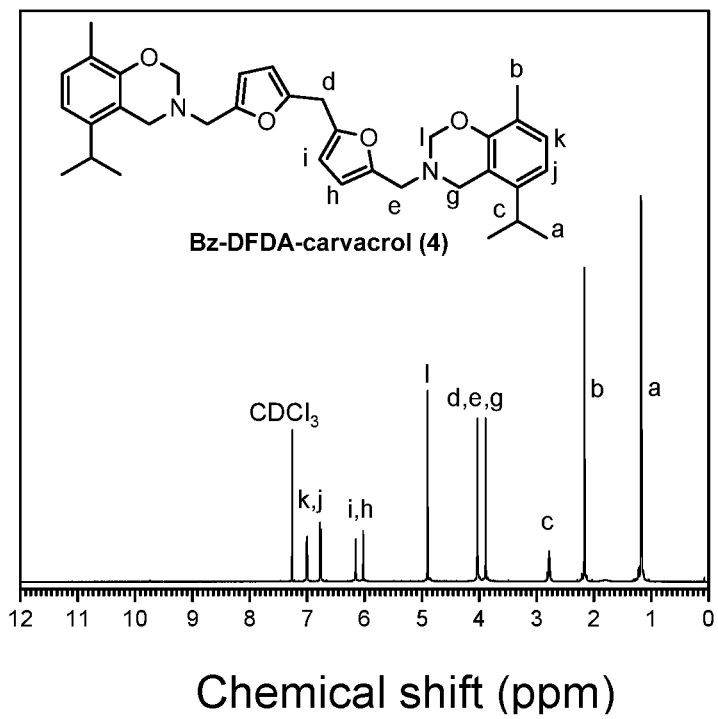
FIG. 4 shows the $^1$H-NMR spectrum of bis(5-((5-isopropyl-8-methyl-2H-benzo[e][1,3]oxazin-3(4H)-yl)methyl)furan-2-yl)methane; (Bz-DFDA-carvacrol)

For illustrative purposes, the principles of the present invention are described by referencing various exemplary embodiments thereof Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The terms "a" (or "an"), "one or more" and "at least one" can be used interchangeably herein. It is also to be noted that the terms "comprising", "including", and "having" can be used interchangeably.

The Benzoxazine Compound

The present invention relates to a benzoxazine compound and a method of preparing the benzoxazine compound.

Suitable benzoxazine compounds of the present invention may selected from Formula (I) or Formula (III), wherein Formula (I) has the following structure:

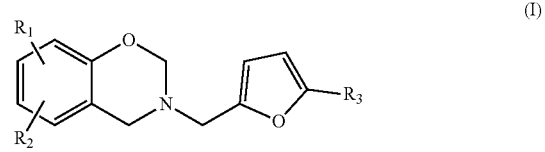

(I)

wherein $R_1$ and $R_2$ in Formula (I) are independently selected from hydrogen, a straight or branched alkyl having 1-4 carbon atoms, a straight or branched alkenyl having 1-4 carbon atoms, a straight or branched alkoxy group having 1-4 carbon atoms and —C(═O)H; $R_3$ is hydrogen or a group having Formula (II):

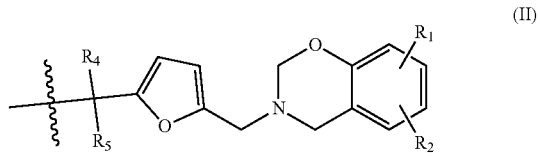

(II)

wherein $R_1$ and $R_2$ in Formula (II) are independently selected from the same groups for $R_1$ and $R_2$ that are defined above, represents the bond to the ring carbon of the furan ring in Formula (I), and $R_4$ in Formula (II) is selected from hydrogen an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms, $R_5$ in Formula (II) is selected from hydrogen an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms wherein $R_4$ and $R_5$ in Formula (II) cannot both be hydrogen;

wherein Formula (III) has the following structure:

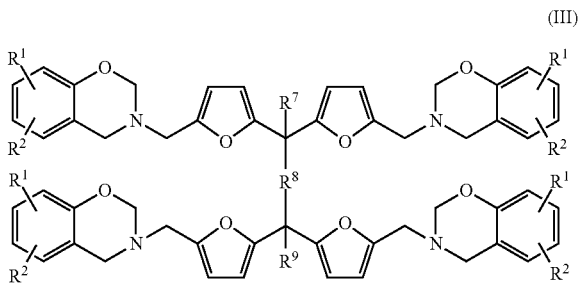

(III)

wherein $R^1$ and $R^2$ in Formula (III) are independently selected from the same groups for $R^1$ and $R^2$ that are defined above, wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, optionally substituted aryl group having 6 to 15 carbon atoms and an optionally substituted cycloalkyl group having 3 to 12 carbon atoms; wherein the alkyl group, alkene group, heterocyclic group, aryl group, or cycloalkyl group can be substituted with 1 to 5 substituents independently selected from a halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted heterocyclic group with 3 to 15 carbon atoms, optionally substituted arylene group having 6 to 15 carbon atoms and an optionally substituted cycloalkylene group having 3 to 12 carbon atoms; wherein the alkylene group, alkenylene group, heterocyclic group, arylene group, or cycloalkylene group can be substituted with 1 to 4 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms.

In other embodiments, $R_1$ and $R_2$ of Formula (1) and $R^1$ and $R^2$ of Formula (III) are independently selected from methyl, isopropyl, methoxy, —C(=O)H and —CH$_2$—CH=CH$_2$ and $R_3$ is hydrogen.

In other embodiments, $R_3$ may be a group having Formula (II) and the benzoxazine compound is symmetrical in that $R_1$ and $R_2$ of Formula (I) are identical to $R_1$ and $R_2$ of Formula (II), respectively.

In other embodiments, $R_1$ and $R_2$ of Formula (I) are not hydrogen and are bonded at the 6-position and the 8-position of the benzoxazine ring, respectively.

In other embodiments, the benzoxazine compound is a compound, wherein (a) $R_1$ and $R_2$ of Formula (I) are not hydrogen and are bonded at the 6-position and 8-position of the benzoxazine ring, respectively, and $R_1$ and $R_2$ of Formula (II) are not hydrogen and are bonded at the 6-position and 8-position of the benzoxazine ring, respectively; or (b) $R_1$ and $R_2$ of Formula (I) are not hydrogen and are bonded at the 5-position and 8-position of the benzoxazine ring, respectively, and $R_1$ and $R_2$ of Formula (II) are not hydrogen and are bonded at the 5-position and 8-position of the benzoxazine ring, respectively.

In other embodiments, $R_4$ and $R_5$ are each independently selected from:

hydrogen, an optionally substituted alkyl group having 7 to 20 carbon atoms, an optionally substituted alkene group having 3 to 20 carbon atoms, an optionally substituted cycloalkyl group having 3 to 12 carbon atoms and an optionally substituted phenyl group, wherein the alkyl group, alkene group, cycloalkyl group or phenyl group can be substituted with 1 to 5 substituents independently selected from an alkyl group having 1-10 carbon atoms, a hydroxyl group, and an alkoxy group having 1 to 20 carbon atoms, wherein both $R_4$ and $R_5$ cannot be hydrogen.

In other embodiments, $R_4$ is hydrogen; $R_5$ is a phenyl group which is optionally substituted with a hydroxyl group, an alkoxy group having 1 to 4 carbon atoms, an alkyl group having 1 to 6 carbon atoms, and an alkene group having 2 to 4 carbon atoms.

In other embodiments, $R_4$ and $R_5$ are each independently selected from hydrogen, an optionally substituted alkyl group having 8 to 18 carbon atoms, an optionally substituted alkene group having 4 to 18 carbon atoms, and an optionally substituted cycloalkyl group having 3 to 8 carbon atoms, wherein the alkyl group, alkene group, or cycloalkyl group can be substituted with 1 to 5 substituents independently selected from a halogen, hydroxy, amino, nitro, cyano, carboxy, an alkyl group having 1 to 8 carbons, and an alkoxy group having 1 to 8 carbon atoms; and wherein only one of $R_4$ and $R_5$ can be a hydrogen.

Non-limiting examples of suitable benzoxazine compounds of the present disclosure include bis(5-((2H-benzo[e][1,3]oxazin-3(4H)-yl)methyl)furan-2-yl)methane; 3,3'-((5,5'-methylenebis(furan-5,2-diyl))bis(methylene))bis(8-methoxy-3,4-dihydro-2H-benzo[e][1,3]oxazine-6-carbaldehyde); 3-(furan-2-ylmethyl)-5-isopropyl-8-methyl-3,4-dihydro-2H-benzo[e][1,3]oxazine; bis(5-((5-isopropyl- 8-methyl-2H-benzo[e][1,3]oxazin-3(4H)-yl)methyl)furan-2-yl)methane; and bis(5-((6-allyl-8-methoxy-2H-benzo[e][1,3]oxazin-3(4H)-yl)methyl)furan-2-yl)methane.

Preferably, the benzoxazine compound is selected from benzoxazine compounds of the present disclosure include bis(5-((2H-benzo[e][1,3]oxazin-3(4H)-yl)methyl)furan-2-yl)methane; 3,3'-((5,5'-methylenebis(furan-5,2-diyl))bis(methylene))bis(8-methoxy-3,4-dihydro-2H-benzo[e][1,3]oxazine-6-carbaldehyde); 3-(furan-2-ylmethyl)-5-isopropyl-8-methyl-3,4-dihydro-2H-benzo[e][1,3]oxazine; bis(5-((5-isopropyl-8-methyl-2H-benzo[e][1,3]oxazin-3(4H)-yl)methyl)furan-2-yl)methane; and bis(5-((6-allyl-8-methoxy-2H-benzo[e][1,3]oxazin-3(4H)-yl)methyl)furan-2-yl)methane.

The benzoxazine compounds of Formula (I) may be prepared by reacting a furfurylamine compound, a formaldehyde compound, and a phenol compound. The following schematic is a reaction mechanism of one way the benzoxazines may be prepared:

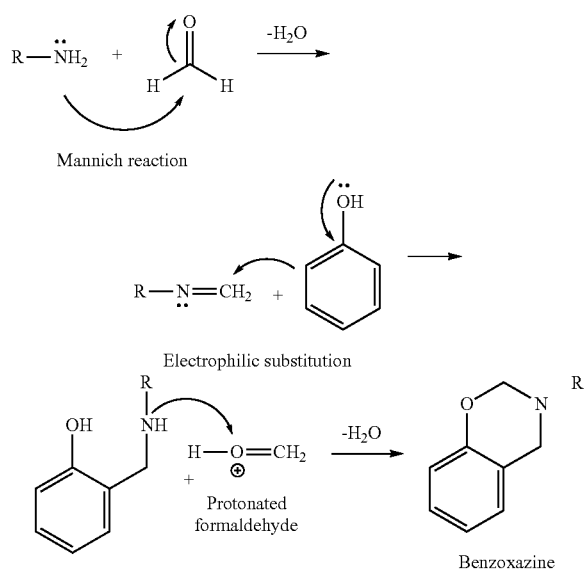

Suitable examples of the phenol compound may be selected from phenol, bisphenol A, bisguaiacol, vanillin, carvacrol, eugenol, 4-hydroxybenzaldehyde, o-cresol, m-cresol, 1,3,5-xylenol. Preferably, the phenol compound is selected from phenol, vanillin, carvacrol and eugenol.

Suitable furfurylamine compounds for making the benzoxazine compound of Formula (I) are compounds according to the Formula (IV) or compounds according to the Formula (V), wherein the compound of Formula (IV) is a difuran diamine compound having the following structure:

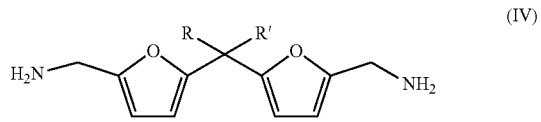

(IV)

wherein R and $R^1$ are independently selected from hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms, wherein only one of R and $R^1$ can be hydrogen;

the compound of Formula (V) is a tetrafuran tetramine compound with the following structure,

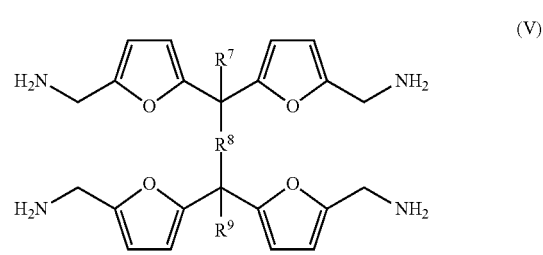

(V)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, optionally substituted aryl group having 6 to 15 carbon atoms and an optionally substituted cycloalkyl group having 3 to 12 carbon atoms; wherein the alkyl group, alkene group, heterocyclic group, aryl group, or cycloalkyl group can be substituted with 1 to 5 substituents independently selected from a halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted heterocyclic group with 3 to 15 carbon atoms, optionally substituted arylene group having 6 to 15 carbon atoms and an optionally substituted cycloalkylene group having 3 to 12 carbon atoms; wherein the alkylene group, alkenylene group, heterocyclic group, arylene group, or cycloalkylene group can be substituted with 1 to 4 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms.

Suitable formaldehyde compounds may be selected from formaldehyde and paraformaldehyde.

The method of preparing the benzoxazine compound may further include use of an inert organic solvent and heating the reaction mixture comprising the furfurylamine compound, the formaldehyde compound, and the phenol compound at a temperature of from 60° C. to 85° C., or from 65° C. to 80° C.

Suitable inert organic solvents may be selected from an aliphatic or cycloaliphatic alcohol, an ester, a ketone, an aromatic or aliphatic hydrocarbon, a halogenated hydrocarbon and a mixture of one or more of the foregoing solvents. Preferably, the inert organic solvent is a halogenated hydrocarbon. Even more preferably, the halogenated hydrocarbon is selected from chloroform and methylene chloride.

In other embodiments of the benzoxazine compound and method of preparing the compound, in $R_1$, $R_2$ and $R_3$ of Formula (I), $R_1$, $R_2$, $R_4$ and $R_5$ of Formula (II), $R_1$, $R_2$, $R_7$ and $R_9$ of Formula (III), R and $R_1$ of Formula (IV), $R_7$ and $R_9$ of Formula (V), $R_1$, $R_2$ and $R_3$ of Formula (VII), $R_1$, $R_2$ and $R_3$ of Formula (VIII), $R_1$ and $R_2$ of Formula (IX), and $R_1$ and $R_2$ of Formula (X):
- the alkyl group is selected from a straight or branched chain butyl, pentyl, hexyl, heptyl, octyl, nonyl, decyl, undecyl and dodecyl,
- the alkene group is selected from a vinyl, propenyl, or a straight or branched chain butenyl, pentenyl, hexenyl, heptenyl, octenyl, nonenyl, decenyl, undecenyl and dodecenyl,
- the cycloalkyl group is selected from a cyclopentyl or cyclohexyl,
- the aryl group is selected from phenyl, tolyl, and biphenyl,
- the heterocyclic group is selected from pyrrolidine, pyrrole, tetrahydrofuran, furan, tetrahydrothiophene, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, piperidine, pyridine, bipyridine, tetrahydropyran, pyran, piperazine, diazines, morpholine, oxazine, thiomorpholine, and thiazine; and
wherein in $R_5$ of Formula (III), $R_5$ of Formula (V), and $R_6$ of Formula (VI):
- the alkylene group is selected from a straight or branched chain butylene, pentylene, hexylene, heptylene, octylene, nonylene, decylene, undecylene and dodecylene,
- the alkenylene group is selected from a vinylene, propenylene, or a straight or branched chain butenylene, pentenylene, hexenylene, heptenylene, octenylene, nonenylene, decenylene, undecenylene and dodecenylene,
- the cycloalkylene group is selected from a cyclopentylene or cyclohexylene,
- the arylene group is selected from phenylene, tolylene, and biphenylene; and wherein the groups are optionally substituted with 1-4 substituents and the optional substituents are selected from group consisting of an alkyl group having 1 to 3 carbons, an aldehyde, a hydroxyl group and methoxy group.

Polymers

The present invention also relates to polymers formed from the benzoxazine compounds. In one embodiment, the polymer may be formed by ring opening polymerization of at least one benzoxazine compound according to Formula (I) or Formula (III) as set forth above, and optionally including an epoxidation reaction with a diepoxide of Formula (VI):

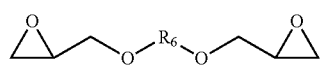

(VI)

wherein $R_6$ is an alkylene group having 1 to 20 carbon atoms, an alkenylene group having 2 to 20 carbon atoms, an heterocyclic group with 3 to 15 carbon atoms, an arylene group having 6 to 15 carbon atoms and a cycloalkylene group having 3 to 12 carbon atoms; wherein the alkylene group, alkenylene group, heterocyclic group, arylene group, or cycloalkylene group can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms. Preferably, the epoxy group-containing compound is bisphenol-A diglycidyl ether (DGEBA) epoxy resin compound or an oligomer thereof.

In another embodiment, the polymer may be formed by ring opening polymerization of at least one benzoxazine compound according to Formula (I) or Formula (III) as set forth above, and optionally including an epoxidation reaction with an epoxide selected from the group consisting of dibisphenol A epoxy resin, bisphenol F epoxy resin, novolac epoxy resin, aliphatic epoxy resin, glycidylamine epoxy resin, phenyl glycidyl ether, tetraglycidyl 4,4'-diaminodiphenylmethane, diepoxide having a phenyl-sulfone-phenyl group, and diglycidyl ether having a Bisphenol B, C, D, or E group. Preferably, the epoxy group-containing compound is bisphenol-A diglycidyl ether (DGEBA) epoxy resin compound or an oligomer thereof.

In another embodiment, the polymer may comprise at least one repeating unit selected from the unit of Formula (VII) and the unit of Formula (VIII):

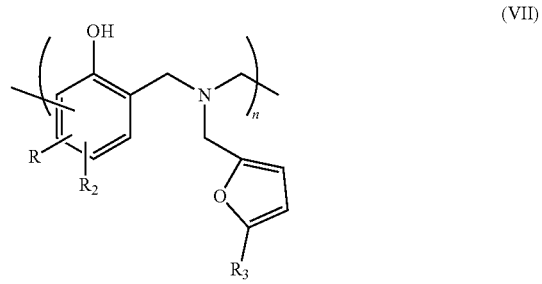

(VII)

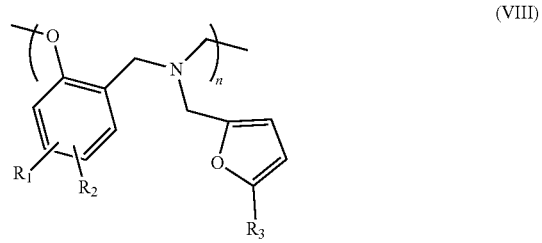

(VIII)

wherein $R_1$ and $R_2$ in Formulae (VII) and (VIII) are independently selected from hydrogen, a straight or branched alkyl, alkenyl, or alkoxy group having 1-4 carbon atoms and —C(=O)H, n is up to 1000; and $R_3$ is hydrogen, or at least one group of the Formula (II) as set forth above, the Formula (IX) and the Formula (X):

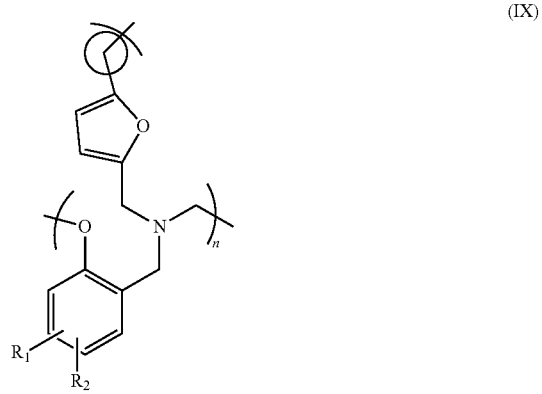

(IX)

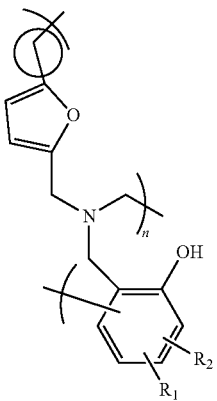

(X)

wherein R₁ and R₂ in Formulae (IX) and (X) are independently selected from hydrogen, a straight or branched alkyl, alkenyl, or alkoxy group having 1-4 carbon atoms and —C(=O)H, n is up to 1000,
wherein the circled methylene group in Formula (IX) and Formula (X) is optionally substituted with R₄ and R₅ or R₇ and R₉ as set forth above.

In another embodiment, in R₁, R₂ and R₃ of Formula (I), R₁, R₂, R₄ and R₅ of Formula (II), R₁, R₂, R₇ and R₉ of Formula (III), R and R₁ of Formula (IV), R₇ and R₉ of Formula (V), R₁, R₂ and R₃ of Formula (VII), R₁, R₂ and R₃ of Formula (VIII), R₁ and R₂ of Formula (IX), and R₁ and R₂ of Formula (X)

the alkyl group is selected from a straight or branched chain butyl, pentyl, hexyl, heptyl, octyl, nonyl, decyl, undecyl and dodecyl,
the alkene group is selected from a vinyl, propenyl, or a straight or branched chain butenyl, pentenyl, hexenyl, heptenyl, octenyl, nonenyl, decenyl, undecenyl and dodecenyl,
the cycloalkyl group is selected from a cyclopentyl or cyclohexyl,
the aryl group is selected from phenyl, tolyl, and biphenyl,
the heterocyclic group is selected from pyrrolidine, pyrrole, tetrahydrofuran, furan, tetrahydrothiophene, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, piperidine, pyridine, bipyridine, tetrahydropyran, pyran, piperazine, diazines, morpholine, oxazine, thiomorpholine, and thiazine; and wherein in R₅ of Formula (III), R₅ of Formula (V), and R₆ of Formula (VI)
the alkylene group is selected from a straight or branched chain butylene, pentylene, hexylene, heptylene, octylene, nonylene, decylene, undecylene and dodecylene,
the alkenylene group is selected from a vinylene, propenylene, or a straight or branched chain butenylene, pentenylene, hexenylene, heptenylene, octenylene, nonenylene, decenylene, undecenylene and dodecenylene,
the cycloalkylene group is selected from a cyclopentylene or cyclohexylene,
the arylene group is selected from phenylene, tolylene, and biphenylene; and
wherein the groups are optionally substituted with 1-4 substituents and the optional substituents are selected from group consisting of an alkyl group having 1 to 3 carbons, an aldehyde, a hydroxyl group and methoxy group.

In one aspect of the invention, the present invention relates to a polymer composition comprising the polymer as set forth above, further including one or more of fiber, clays, silicates, fillers, whiskers, pigments, corrosion inhibitors, flow additives, film formers, defoamers, coupling agents, antioxidants, stabilizers, flame retardants, reheating aids, plasticizers, flexibilizers, anti-fogging agents, nucleating agents, or combinations thereof Preferably, the polymer composition comprises a pigment, a corrosion inhibitor, and fibers.

Suitable pigments may be selected from titanium dioxides, iron oxides, carbon black and mixtures thereof. Preferably, the corrosion inhibitor is zinc phosphate and the fibers are glass fibers.

The polymers of the present invention may have a glass transition temperature range of from 100° C. to 300° C., or from 120° C. to 280° C., or from 170° C. to 275° C.

The polymers may have a flexural modulus ranges from 2 GPa to 4 GPa at room temperature, or from 2.2 GPa to 3.8 GPa at room temperature, or from 2.5 GPa to 3.7 GPa at room temperature.

The polymers of the present invention may have a flexural strength is greater than 20 MPa at room temperature, or greater than 22 MPa at room temperature, or greater than 25 MPa at room temperature.

The polymers of the present invention may have a UL-94 flammability (standard of 2017) of V-0 or V-1 rating.

Preparation of Molding Compositions

In another aspect of the invention, the benzoxazine-containing compound may be used to prepare benzoxazine-containing molding compositions, which can be prepared by any conventional methods. For example, the materials (including resins and other additives) can be finely ground, dry blended, densified on a hot differential roll mill, and then followed by granulation. The molding composition, as described above, can be used for coating electronic devices such as semiconductors or circuit boards. The prepared compositions can be molded by any suitable molding apparatus. An example of such an apparatus is a transfer press equipped with a multi-cavity mold. For more detail on methods for preparing molding compositions and for coating electronic devices, see U.S. Pat. No. 5,476,716.

The following list includes examples of suitable additives that may be included in the molding composition and preferred weight ranges of the additives, based on the total weight percent of the composition:

(1) A flame retardant such as a brominated epoxy novolac flame retardant (e.g., BREN, available from Nippon Kayaku). The preferred molding composition can contain up to 3.0 wt %, more preferably, 0.1-1.0 wt % of a flame retardant.

(2) A flame retardant synergist such as $Sb_2O_5$ or $WO_3$. The preferred molding composition can contain up to 3.0 wt %, more preferably, 0.25-1.5 wt % of a flame retardant synergist.

(3) A filler such as silica, calcium silicate, and aluminum oxide. The preferred molding composition can contain 70-90 wt. %, more preferably, 75-85 wt % of a filler.

(4) A colorant such as carbon black colorant. The preferred molding composition can contain 0.1-2.0 wt %, more preferably, 0.1-1.0 wt. % of a colorant.

(5) A wax or a combination of waxes such as camauba wax, paraffin wax, S-wax, and E-wax. The preferred molding composition can contain 0.1-2.0 wt. %, more preferably, 0.3-1.5 wt % of a wax.

(6) Fumed silica such as aerosil. The preferred molding composition can contain 0.3-5.0 wt 00 more preferably, 0.7-3.0 wt % of fumed silica.

EXAMPLES

The following examples are illustrative, but not limiting of the methods and compositions of the present disclosure.

The following materials were employed throughout the examples. Furfurylamine (99%), guaiacol (98%), carvacrol (98%), eugenol (99%), vanillin (99%), paraformaldehyde (95%), phenol (99%), (hydrochloric acid (37%), chloroform, sodium hydroxide (98%) and tetrahydrofuran (THF, 99.9%) were supplied by Sigma-Aldrich, USA. All chemicals were used as received. 5,5'-methylenedifurfurylamine (DFDA) was synthesized according to the literature method [15].

The following schematic shows a general reaction mechanism for preparing benzoxazines compounds:

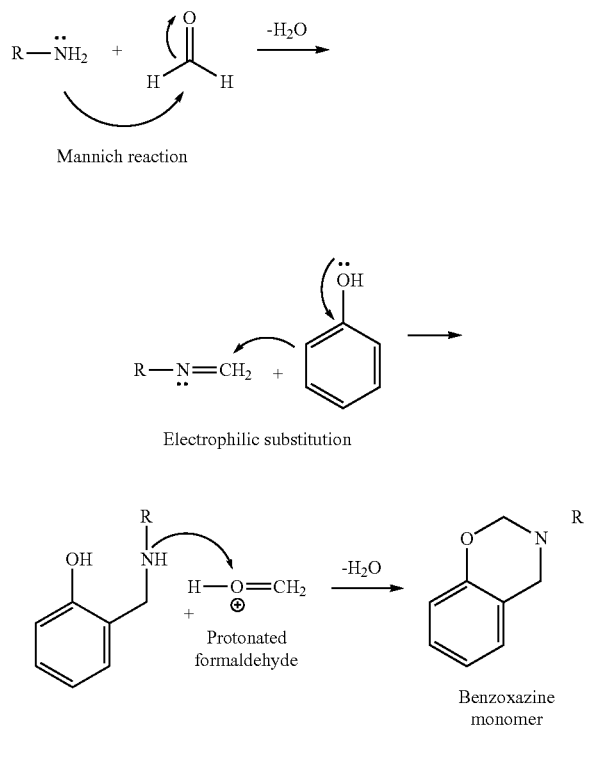

Preparation of Renewable Benzoxazine Monomers

Example 1

Preparation of bis(5-((2H-benzo[e][1,3]oxazin-3 (4H)-yl)methyl)furan-2-yl)methane; (Bz-DFDA-phenol) (1)

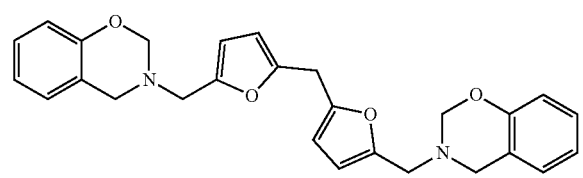

Bz-DFDA-phenol (1)

5,5'-methylenedifurfurylamine (DFDA) (2 g, 9.71 mmol) and paraformaldehyde (1.166 g, 38.84 mmol) and chloroform (20 mL) were stirred in a round-bottomed flask at room temperature for 30 min. After that phenol (1.827 g, 19.42 mmol) was slowly added. The reaction mixture was heated to 70° C. and refluxed for 20 h. A brownish viscous liquid solution was obtained. The solution was washed several times with 0.1 M NaOH aqueous solution and distilled water. The solution was precipitated in diethyl ether, filtered, and dried under vacuum to obtain Bzs as a brown solid. $^1$H NMR (500 MHz, CDCl$_3$, ppm): δ 7.15 (d, 2H); 6.94 (d, 2H); 6.88 (d, 2H); 6.79 (m, 2H); 6.17 (d, 2H); 6.03 (d, 2H); 4.90 (s, 4H); 4.03 (s, 4H); 3.99 (s, 4H); 3.87 (s, 2H).

Example 2

Preparation of 3,3'-((5,5'-methylenebis(furan-5,2-diyl))bis(methylene))bis(8-methoxy-3,4-dihydro-2H-benzo[e][1,3]oxazine-6-carbaldehyde); (Bz-DFDA-vanillin) (2)

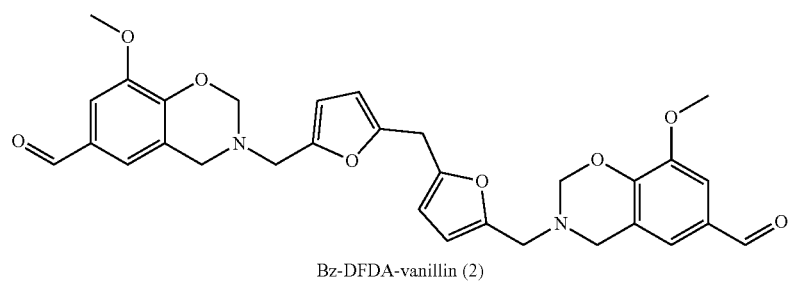 [SMILES: COc1cc(C=O)cc2c1OCN(Cc1ccc(Cc3ccc(CN4COc5c(cc(C=O)cc5OC)C4)o3)o1)C2]

Bz-DFDA-vanillin (2)

5,5'-methylenedifurfurylamine (DFDA) (2 g, 9.71 mmol) and paraformaldehyde (1.166 g, 38.84 mmol) and chloroform (20 mL) were stirred in a round-bottomed flask at room temperature for 30 min. After that vanillin (2.954 g, 19.42 mmol) was slowly added. The reaction mixture was heated to 70° C. and refluxed for 20 h. A brownish viscous liquid solution was obtained. The solution was washed several times with 0.1 M NaOH aqueous solution and distilled water. The organic phase was precipitated in diethyl ether and dried under vacuum to obtain Bzs as a yellow powder. $^1$H NMR (500 MHz, CDCl$_3$, ppm): δ 9.82 (s, 2H); 7.45 (s, 2H); 7.15 (s, 2H); 6.19 (d, 2H); 6.03 (d, 2H); 5.03 (s, 4H); 4.10 (s, 6H); 3.98 (s, 4H); 3.94 (s, 4H); 3.89 (s, 2H).

Example 3

Preparation of 3-(furan-2-ylmethyl)-5-isopropyl-8-methyl-3,4-dihydro-2H-benzo[e][1,3]oxazine; (Bz-FA-carvacrol) (3)

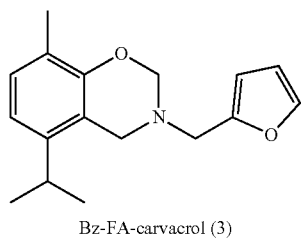 [SMILES: Cc1ccc(C(C)C)c2c1OCN(Cc1ccco1)C2]

Bz-FA-carvacrol (3)

Furfurylamine (5 g, 58.48 mmol), paraformaldehyde (3.091 g, 102.965 mmol) and carvacrol (7.73 g, 102.965 mmol) were mixed and stirred at room temperature. The mixture was refluxed at 70° C. for 20 h, cooled to room temperature, and concentrated under reduced pressure to obtain Bzf as a yellow solid. $^1$H NMR (500 MHz, CDCl$_3$, ppm): δ 7.44 (d, 1H); 7.01 (d, 1H); 6.76 (d, 1H); 6.35 (m, 1H); 6.23 (d, 1H); 4.91 (s, 2H); 4.02 (s, 2H); 3.92 (s, 2H); 2.78 (m, 1H); 2.17 (s, 3H); 1.17 (d, 6H).

Example 4

Preparation of bis(5-((5-isopropyl-8-methyl-2H-benzo[e][1,3]oxazin-3(4H)-yl)methyl)furan-2-yl)methane; (Bz-DFDA-carvacrol) (4)

Bz-DFDA-carvacrol (4)

5,5'-methylenedifurfurylamine (DFDA) (2 g, 9.71 mmol) and paraformaldehyde (1.166 g, 38.84 mmol) and chloroform (20 mL) were stirred in a round-bottomed flask at room temperature for 30 min. After that carvacrol (2.916 g, 19.42 mmol) was slowly added. The reaction mixture was heated to 70° C. and refluxed for 20 h. A brownish viscous liquid solution was obtained. The solution was washed several times with 0.1 M NaOH aqueous solution and distilled water. The organic phase was precipitated in methanol and filtered and dried under vacuum to obtain Bzs as a yellow powder. $^1$H NMR (500 MHz, CDCl$_3$, ppm): δ 7.0 (d, 2H); 6.96 (d, 2H); 6.15 (d, 2H); 6.01 (d, 2H); 4.91 (s, 4H); 4.03 (s, 4H); 3.88 (s, 4H); 2.78 (s, 2H); 2.17 (s, 6H); 1.18 (d, 12H).

Example 5

Preparation of bis(5-((6-allyl-8-methoxy-2H-benzo[e][1,3]oxazin-3(4H)-yl)methyl)furan-2-yl)methane; (Bz-DFDA-eugenol) (5)

Bz-DFDA-eugenol (5)

5,5'-methylenedifurfurylamine (DFDA) (2 g, 9.71 mmol) and paraformaldehyde (1.166 g, 38.84 mmol) and chloroform (20 mL) were stirred in a round-bottomed flask at room temperature for 30 min. After that eugenol (2.954 g, 19.42 mmol) was slowly added. The reaction mixture was heated to 70° C. and refluxed for 20 h. A brownish viscous liquid solution was obtained. The solution was washed several times with 0.1 M NaOH aqueous solution and distilled water. The organic phase was dried over anhydrous MgSO4 and the solvent was removed. The residual solid obtain Bzs as a yellow powder. $^1$H NMR (500 MHz, CDCl$_3$, ppm): δ 7.15 (d, 2H); 6.78 (d, 2H); 6.17 (d, 2H); 6.05 (d, 2H); 5.92 (m, 2H); 5.01 (s, 4H); 5.04 (s, 2H); 4.79 (d, 2H); 3.83 (s, 6H); 3.76 (s, 4H); 3.70 (s, 4H); 3.51 (s, 2H); 3.33 (d, 4H).

Preparation of Benzoxazine/Glass Fiber Composites

The thermal profiles obtained from the DMA measurement of benzoxazine and glass fiber composites showed curing kinetic behavior of polyimide composites. The initial sharp initial loss of storage modulus benzoxazine/glass fiber composites results from the melt of the monomers. It is evident that the chemical reaction leading to chain extension does not occur below 100° C. It suggest that the furan-based benzoxazine monomers have large temperature window for processing of resin systems. Further, the storage modulus of benzoxazine/glass fiber composites tends to increase at higher temperature, which reflect the occurrence of thermally activated chemical reactions within the matrix networks lead to further crosslinking and other form of matrix developments.

Material Characterization

Mid-IR was used to identify functional groups on the benzoxazines using a Thermo Nicolet Nexus 870 FT-IR spectrometer in absorbance mode with 32 scans and an 8 cm$^{-1}$ resolution at RT with a deuterated tryglycine sulfate (DTGS) detector in 650-4000 cm$^{-1}$ range. Dynamic mechanical analysis (DMA) and thermogravimetric analysis (TGA) were used to investigate the thermal and mechanical properties of cured samples. DMA samples were tested using a TA Q800 DMA in single cantilever geometry with a 1 Hz frequency, 15 μm amplitude and 2° C./min ramp rate from 25 to 400° C. Each sample was tested twice and the first and second both scan were reported, the first scan was used to obtain its glass transition temperature ($T_g$). A TA Q50 TGA was employed to investigate the thermal stability of samples in argon and air environment by heating from 25° C. to 800° C. with 1° C./min ramp rate.

Figure 5:
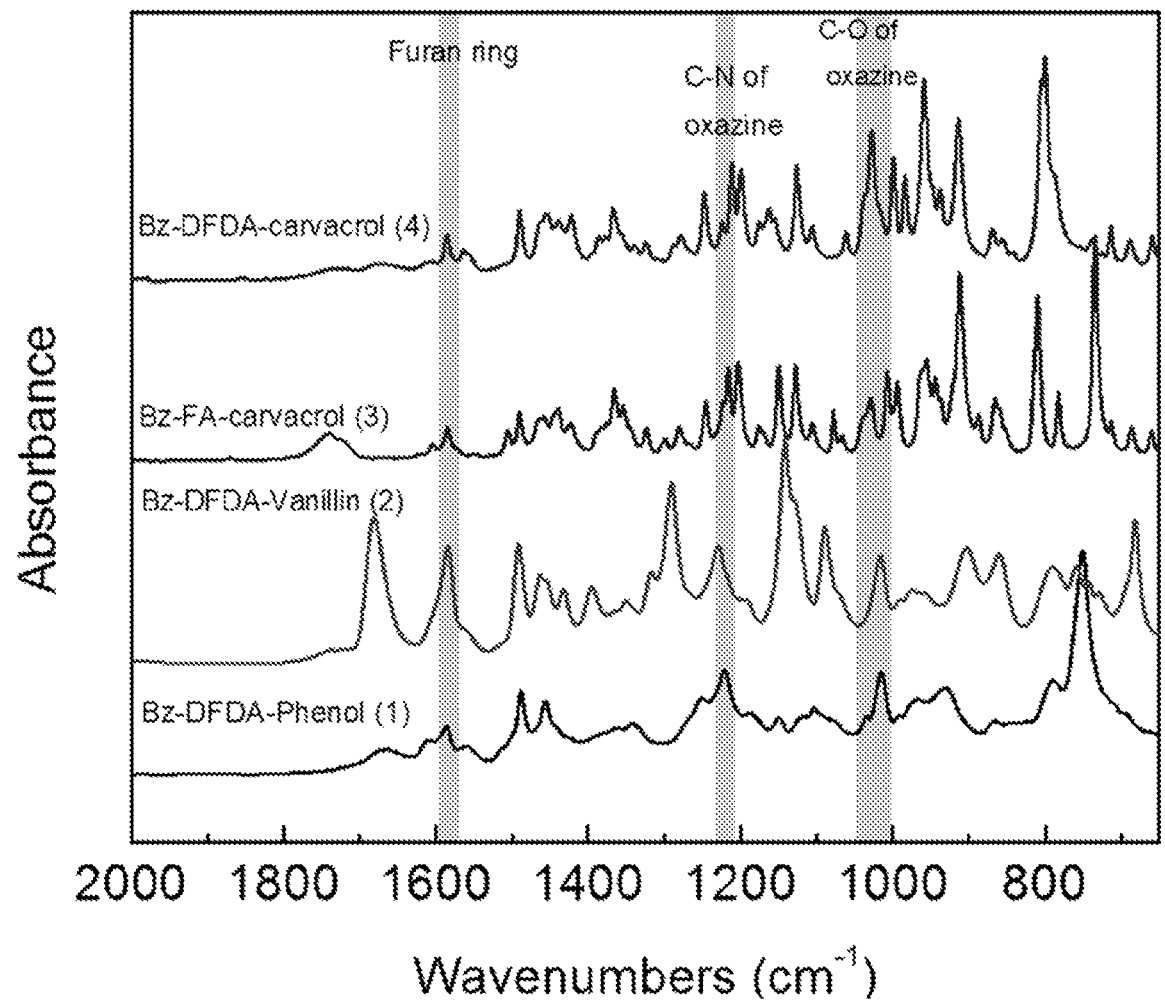
FIG. 5 shows the Fourier-transform infrared (FTIR) spectra of the benzoxazine monomers.
Figure 6:
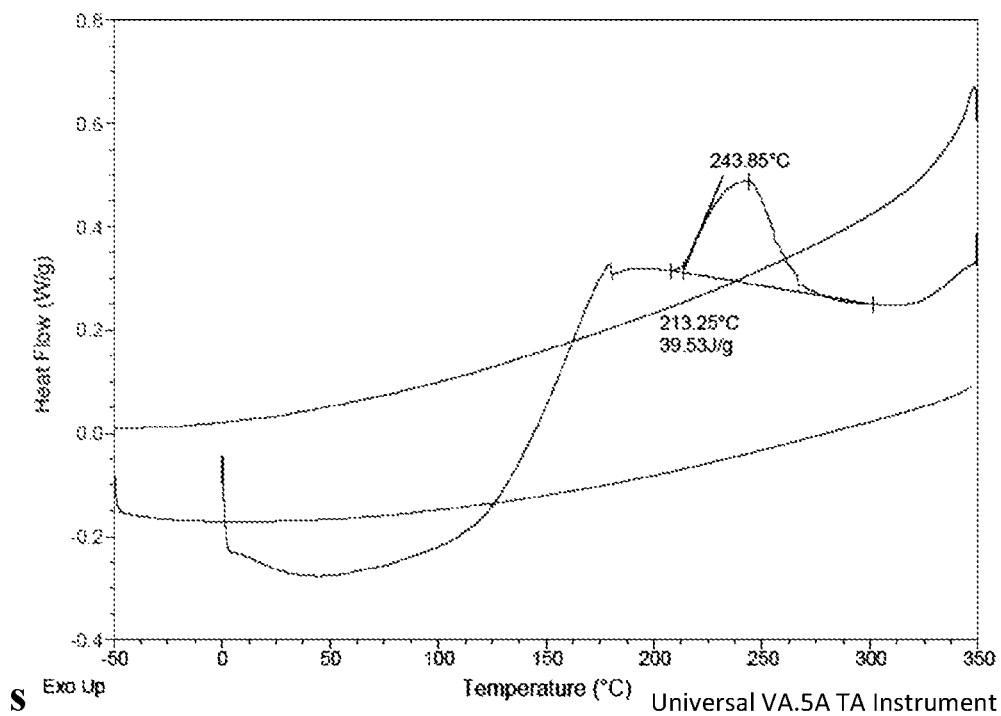
FIG. 6 shows the Differential scanning calorimetry (DSC) curves of the BZ-DFDA-phenol monomer.
Figure 7:
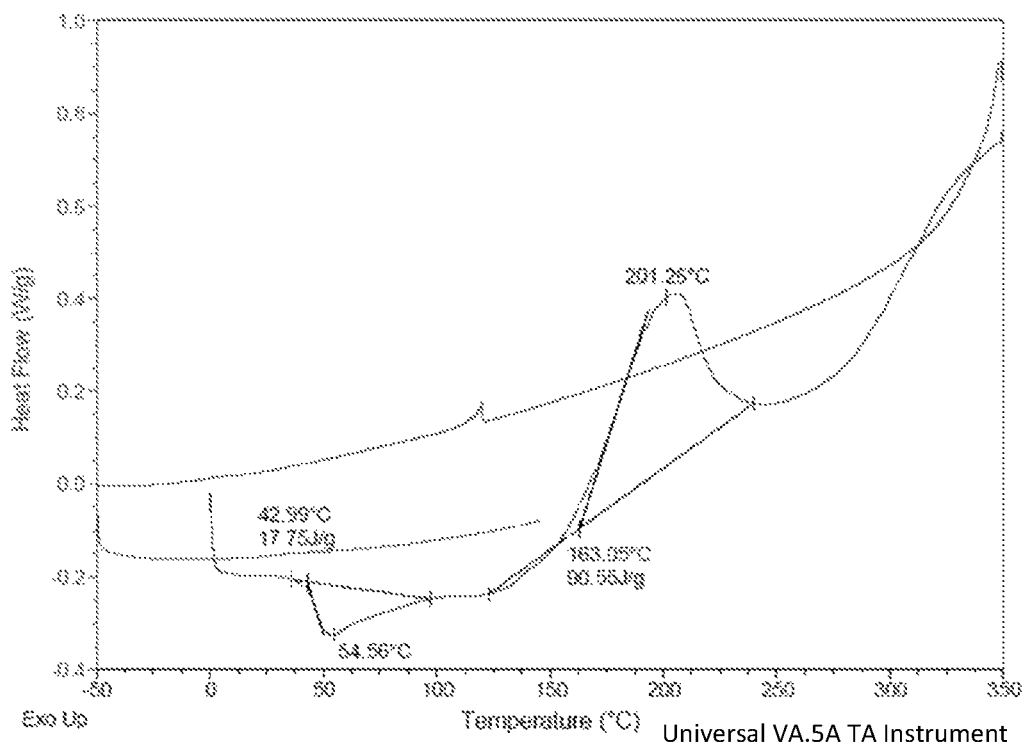
FIG. 7 shows the Differential scanning calorimetry (DSC) curves of the BZ-DFDA-vanillin monomer.
Figure 8:
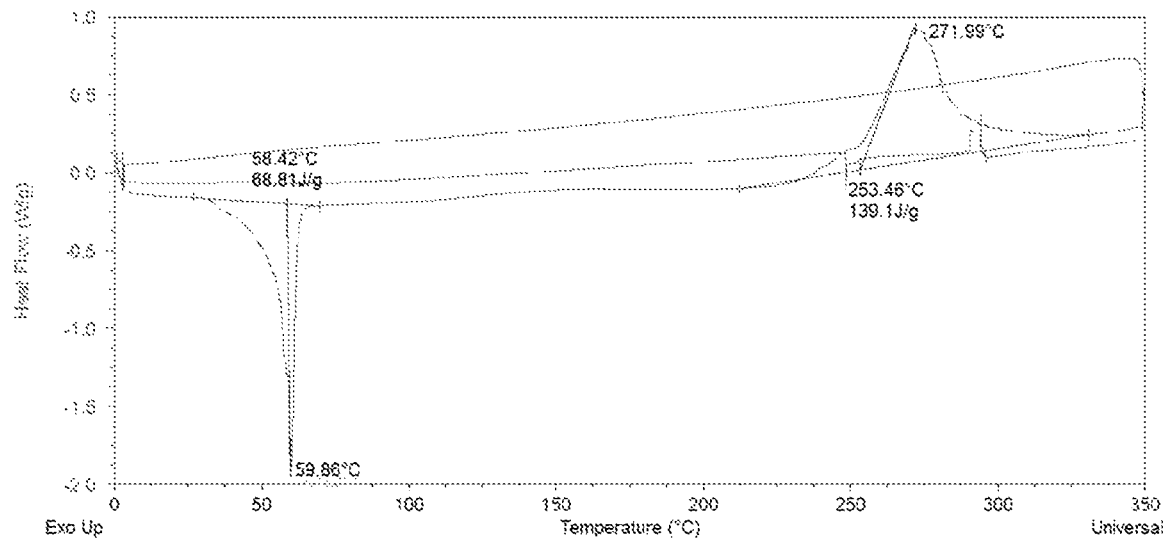
FIG. 8 shows the Differential scanning calorimetry (DSC) curves of the BZ-FA-carvacrol monomer.
Figure 9:
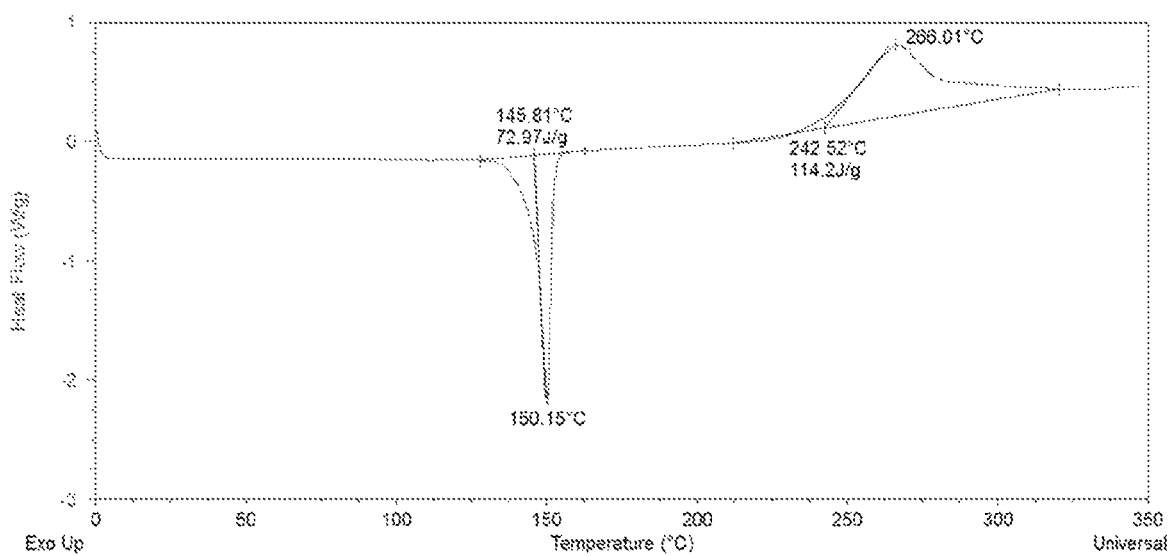
FIG. 9 shows the Differential scanning calorimetry (DSC) curves of the BZ-DFDA-carvacrol monomer.
Figure 10:
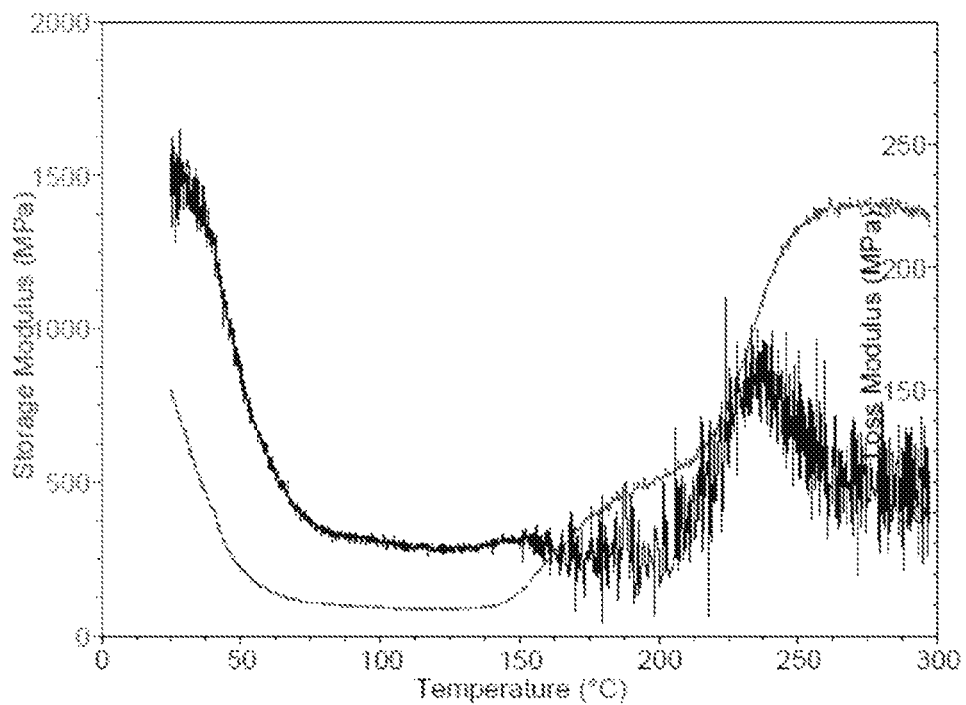
FIG. 10 shows the Dynamic mechanical analysis (DMA) data of the BZ-DFDA-phenol/glass fiber composites.
Figure 11:
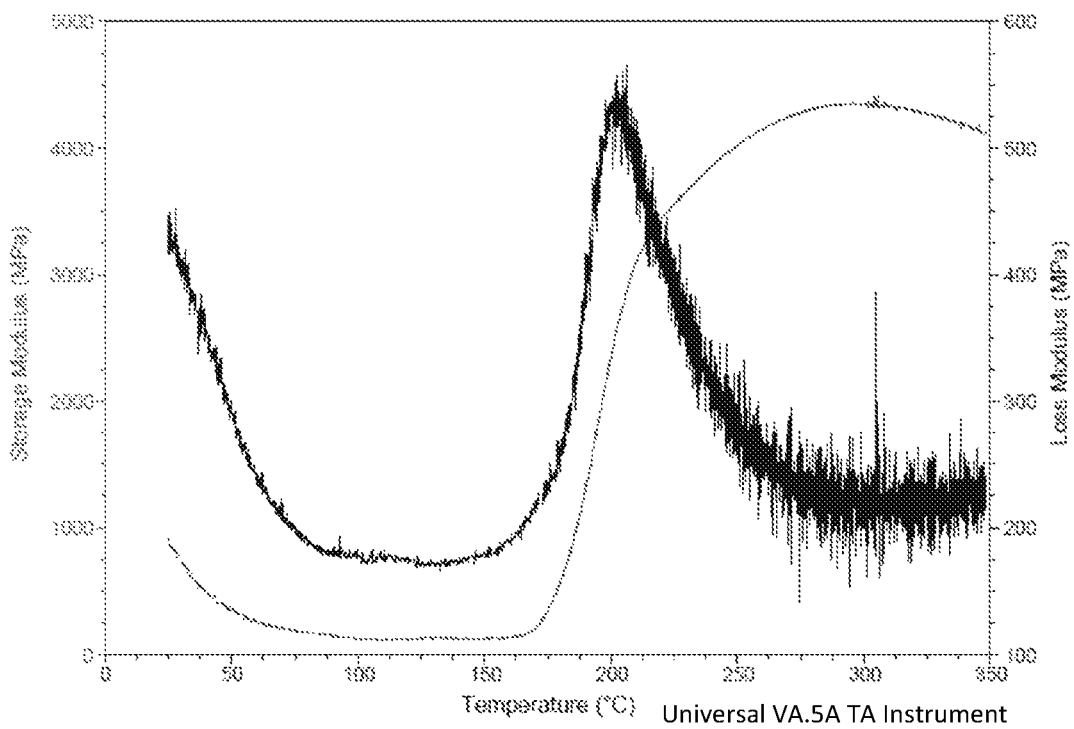
FIG. 11 shows the Dynamic mechanical analysis (DMA) data of the BZ-DFDA-vanillin/glass fiber composites.
Figure 12:
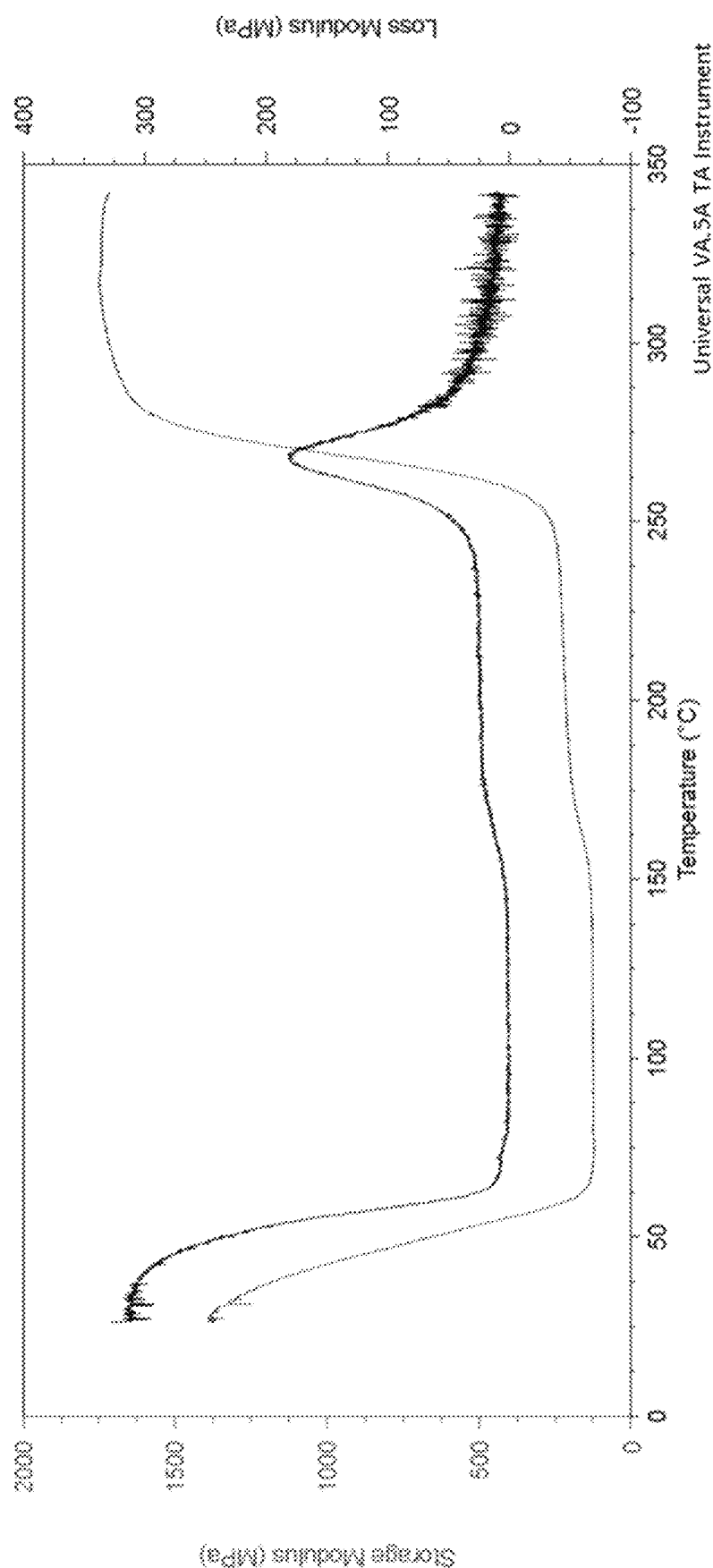
FIG. 12 shows the Dynamic mechanical analysis (DMA) data of the BZ-FA-carvacrol/glass fiber composites.
Figure 13:
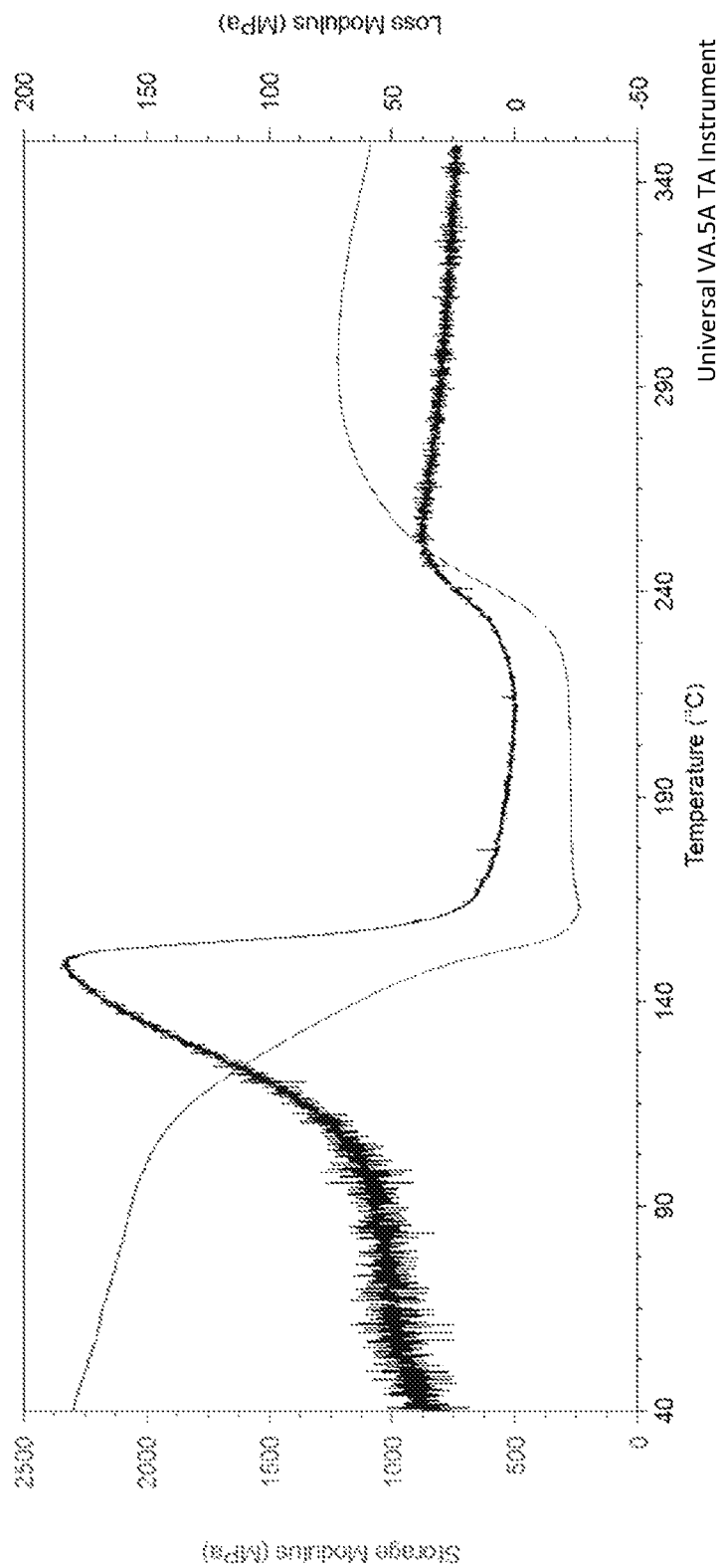
FIG. 13 shows the Dynamic mechanical analysis (DMA) data of the BZ-DFDA-carvacrol/glass fiber composites.

The structures of the novel biobased benzoxazine monomers are supported by the IR spectra shown in FIG. 5. The oxazine ring is indicated by the aromatic C—O—C between 1220 cm$^1$ and 1235 cm$^{-1}$ and aliphatic C—N stretching at 1020 cm$^{-1}$, indicating the formation of an oxazine ring fused to the benzene ring. The characteristic peaks attributable to the furan ring of Bzf are observed at 1584 cm-1 for all the biobased benzoxazine. The monomer BZ-DFDA-vanillin displayed the peak at 1686 cm$^{-1}$ for the C=O stretching of carbonyl. The BZ-DFDA-carvacrol and BZ-FA-carvacrol show the distinguish peak at 1359 cm-1 due to the isopropyl group. As can be seen FIG. 6, BZ-DFDA-phenol does not show the melt endotherm. The BZ-DFDA Vanillin, BZ-FA-carvacrol, BZ-DFDA-carvacrol benzoxazine monomers exhibit melting endotherms 55, 60 and 150° C. respectively. A significant influence of the monomer structure on melting temperatures is observed. In addition to melting endotherm, all benzoxazine monomers present a relatively broad range of exothermic peak between 200 and 275° C. which is characteristic for the curing process of conventional non-activated.

The exothermic final for the BZ-DFDA-phenol, BZ-DFDA-vanillin, BZ-FA-carvacrol and BZ-DFDA-carvacrol monomers was observed at 242, 201, 266 and 271° C., respectively (FIGS. 6-9). It is well known that ring-opening polymerization of benzoxazine will exhibit an exothermic peak around 200-280° C. The biobased benzoxazines monomers also demonstrated a similar exothermic manners in the high-temperature range. The processing window is defined as the temperature difference between the melting point and onset of polymerization. All the monomer shows a wide processing window.

The thermal profiles obtained from the DMA measurement of benzoxazine monomers and glass fiber composites showed curing kinetic behavior of benzoxazine composites (FIGS. 10-13). The initial sharp loss of storage modulus of Bz-DFDA-phenol/glass fiber, Bz-DFDA-vanillin/glass fiber and Bz-FA-carvacrol/glass fiber around 40-60° C. results from the melt of the monomers. However, the higher (150° C.) initial loss of storage modulus was observed for Bz-DFDA-carvacrol/glass fiber composites. It is evident that the chemical reaction leading to chain extension does not occur below 100° C. Further the storage modulus of Bz-DFDA-phenol/glass fiber, Bz-DFDA-vanillin/glass fiber, Bz-FA-carvacrol/glass fiber, and Bz-DFDA-carvacrol/glass fiber composites tends to increase around 140, 165, 250 and 235° C. respectively, which reflect the occurrence of thermally activated chemical reactions within the matrix networks lead to further crosslinking and other form of matrix developments. Which matches with the DSC data and it suggest that the furan-based benzoxazines have large temperature windows for processing of resin systems.

REFERENCES

The following references may be useful in understanding some of the principles discussed herein:

[1] Lligadas G, Tuzun A, Ronda J C, Galia M, Cadiz V. Polybenzoxazines: new players in the bio-based polymer arena. Polymer Chemistry. 2014; 5:6636-44.

[2] Takeichi T, Kawauchi T, Agag T. High Performance Polybenzoxazines as a Novel Type of Phenolic Resin. Polym J. 2008; 40:1121-31.

[3] Ghosh N N, Kiskan B, Yagci Y. Polybenzoxazines-New high performance thermosetting resins: Synthesis and properties. Progress in Polymer Science. 2007; 32:1344-91.

[4] Sini N K, Bijwe J, Varma I K. Renewable benzoxazine monomer from Vanillin: Synthesis, characterization, and studies on curing behavior. Journal of Polymer Science Part A: Polymer Chemistry. 2014; 52:7-11.

[5] Kotzebue LRV, Ribeiro F W M, Sombra V G, Feitosa J P A, Mele G, Mazzetto S E, et al. Spectral and thermal studies on the synthesis and catalyzed oligomerization of novel cardanol-based benzoxazines. Polymer. 2016; 92:189-200.

[6] Baroncini E A, Kumar Yadav S, Palmese G R, Stanzione J F. Recent advances in bio-based epoxy resins and bio-based epoxy curing agents. Journal of Applied Polymer Science. 2016; 133:n/a-n/a.

[7] Puchot L, Verge P, Fouquet T, Vancaeyzeele C, Vidal F, Habibi Y. Breaking the symmetry of dibenzoxazines: a paradigm to tailor the design of bio-based thermosets. Green Chemistry. 2016; 18:3346-53.

[8] Sini N K, Bijwe J, Varma I K. Thermal behaviour of bis-benzoxazines derived from renewable feed stock 'vanillin'. Polymer Degradation and Stability. 2014; 109: 270-7.

[9] Froimowicz P, R. Arza C, Han L, Ishida H. Smart, Sustainable, and Ecofriendly Chemical Design of Fully Bio-Based Thermally Stable Thermosets Based on Benzoxazine Chemistry. ChemSusChem. 2016; 9:1921-8.

[10] Periyasamy T, Asrafali S P, Muthusamy S. New benzoxazines containing polyhedral oligomeric silsesquioxane from eugenol, guaiacol and vanillin. New Journal of Chemistry. 2015; 39:1691-702.

[11] Wang J, Liu W, Feng T. Chapter 28—Furan-Based Benzoxazines A2—Ishida, Hatsuo. In: Froimowicz P, editor. Advanced and Emerging Polybenzoxazine Science and Technology. Amsterdam: Elsevier; 2017. p. 533-67.

[12] Dumas L, Bonnaud L, Olivier M, Poorteman M, Dubois P. Eugenol-based benzoxazine: from straight synthesis to taming of the network properties. Journal of Materials Chemistry A. 2015; 3:6012-8.

[13] Thirukumaran P, Shakila Parveen A, Sarojadevi M. Synthesis and Copolymerization of Fully Biobased Benzoxazines from Renewable Resources. ACS Sustainable Chemistry & Engineering. 2014; 2:2790-801.

[14] Wang C, Sun J, Liu X, Sudo A, Endo T. Synthesis and copolymerization of fully bio-based benzoxazines from guaiacol, furfurylamine and stearylamine. Green Chemistry. 2012; 14:2799-806.

[15] Hu F, Yadav S K, La Scala J J, Sadler J M, Palmese G R. Preparation and Characterization of Fully Furan-Based Renewable Thermosetting Epoxy-Amine Systems. Macromolecular Chemistry and Physics. 2015; 216:1441-6.

The invention claimed is:

1. A benzoxazine compound of Formula (I):

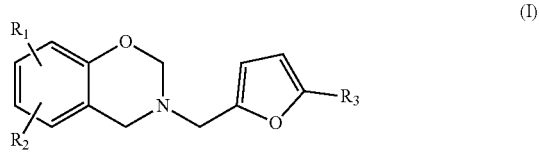

wherein $R_1$ is selected from the group consisting of a straight or branched alkyl having 1-4 carbon atoms, a straight or branched alkenyl having 1-4 carbon atoms, and a straight or branched alkoxy group having 1-4 carbon atoms; and $R_2$ in Formula (I) is selected from the group consisting of hydrogen, a straight or branched alkyl having 1-4 carbon atoms, a straight or branched alkenyl having 1-4 carbon atoms, and a straight or branched alkoxy group having 1-4 carbon atoms; and $R_3$ is a group having Formula (II):

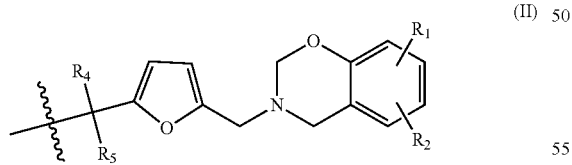

wherein $R_1$ and $R_2$ in Formula (II) are independently selected from the same groups for $R_1$ and $R_2$ that are defined above for Formula (I),

represents the bond to the ring carbon of the furan ring in Formula (I), and $R_4$ in Formula (II) is selected from the group consisting of hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group of $R_4$ can be substituted with 1 to 5 substituents independently selected from the group consisting of halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms, $R_5$ in Formula (II) is selected from the group consisting of hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; wherein the alkyl group, alkene group, cycloalkyl group, aryl group or heterocyclic group of $R_5$ can be substituted with 1 to 5 substituents independently selected from the group consisting of halogen, hydroxy, amino, nitro, cyano, carboxy, an alkyl group having 1 to 20 carbons, an aryl group having 6 to 16 carbon atoms, a heterocyclic group having 3 to 16 carbons, and an alkoxy group having 1 to 20 carbon atoms.

2. The benzoxazine compound of claim 1, wherein $R_1$ of Formula (I) is selected from the group consisting of methyl, isopropyl, methoxy, and —$CH_2$—CH=$CH_2$, and $R_2$ of Formula (I) is selected from hydrogen, methyl, isopropyl, methoxy, and —$CH_2$—CH=$CH_2$.

3. The benzoxazine compound of claim 1, wherein the benzoxazine compound is symmetrical in that $R_1$ and $R_2$ of Formula (I) are identical to $R_1$ and $R_2$ of Formula (II), respectively.

4. The benzoxazine compound of claim 1, wherein $R_1$ of Formula (I) is bonded at the 6-position of the benzoxazine ring; and $R_2$ of Formula (I) is not hydrogen and is bonded at the 8-position of the benzoxazine ring.

5. The benzoxazine compound of claim 1, wherein:

(a) $R_1$ of Formula (I) is selected from the group consisting of methyl, isopropyl, methoxy, and —$CH_2$—CH=$CH_2$, and $R_2$ of Formula (I) is not hydrogen and is selected from the group consisting of methyl, isopropyl, methoxy, and —$CH_2$—CH=$CH_2$, and $R_1$ of Formula (II) is selected from the group consisting of methyl, isopropyl, methoxy, and —$CH_2$—CH=$CH_2$, and $R_2$ of Formula (II) is not hydrogen and is selected from the group consisting of methyl, isopropyl, methoxy, and —$CH_2$—CH=$CH_2$; or (b) $R_1$ of Formula (I) is selected from the group consisting of methyl, isopropyl, methoxy, and —$CH_2$—CH=$CH_2$, and $R_2$ of Formula (I) is hydrogen, and $R_1$ of Formula (II) is selected from methyl, isopropyl, methoxy, and —$CH_2$—CH=$CH_2$, and $R_2$ of Formula (II) is hydrogen.

6. The benzoxazine compound of claim 1, wherein: $R_4$ and $R_5$ are both hydrogen.

7. The benzoxazine compound of claim 1, wherein: $R_4$ is hydrogen; $R_5$ is a phenyl group which is optionally substituted with a group selected from the group consisting of a hydroxyl group, an alkoxy group having 1 to 4 carbon atoms, an alkyl group having 1 to 6 carbon atoms, and an alkene group having 2 to 4 carbon atoms.

8. The benzoxazine compound of claim 1, wherein:

$R_4$ and $R_5$ are each independently selected from the group consisting of:

hydrogen, an optionally substituted alkyl group having 8 to 18 carbon atoms, an optionally substituted alkene group having 4 to 18 carbon atoms, and an optionally substituted cycloalkyl group having 3 to 8 carbon atoms, wherein the alkyl group, alkene group, or cycloalkyl group of $R_4$ and $R_5$ can be substituted with 1 to 5 substituents independently selected from the group consisting of halogen, hydroxy, amino, nitro, cyano, carboxy, an alkyl group having 1 to 8 carbons, and an alkoxy group having 1 to 8 carbon atoms.

9. The benzoxazine compound of claim 1, selected from the group consisting of:
   a. bis(5-((5-isopropyl-8-methyl-2H-benzo[e][1,3]oxazin-3(4H)-yl)methyl) furan-2-yl)methane;
   b. bis(5-((6-allyl-8-methoxy-2H-benzo[e][1,3]oxazin-3(4H)-yl)methyl) furan-2-yl)methane; and
   c. wherein $R_1$ of Formula (I) and Formula (II) is methoxy, $R_2$ of Formula (I) and Formula (II) is hydrogen, and $R_4$ and $R_5$ are hydrogen.

10. The benzoxazine compound of claim 1, wherein $R_1$ of Formula (I) is a straight or branched alkoxy group having 1-4 carbon atoms, and $R_2$ of Formula (I) is hydrogen, and $R_1$ of Formula (II) is a straight or branched alkoxy group having 1-4 carbon atoms, and $R_2$ of Formula (II) is hydrogen.

* * * * *